US012642501B2

(12) United States Patent
Kim et al.

(10) Patent No.: US 12,642,501 B2
(45) Date of Patent: Jun. 2, 2026

(54) ULTRASOUND IMAGING APPARATUS FOR DISPLAYING A KUPFFER PHASE BASED ON CONTRAST-ENHANCED IMAGES

(71) Applicant: SAMSUNG MEDISON CO., LTD., Hongcheon-gun (KR)

(72) Inventors: Mo Se Kim, Hongcheon-Gun (KR); Jun Woo Lim, Seoul (KR); Yoon Chang Lee, Hongcheon-Gun (KR); Jeong Min Lee, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 11 days.

(21) Appl. No.: 18/219,312

(22) Filed: Jul. 7, 2023

(65) Prior Publication Data
US 2024/0245384 A1 Jul. 25, 2024

(30) Foreign Application Priority Data

Jan. 25, 2023 (KR) ......................... 10-2023-0009720
Apr. 25, 2023 (KR) ......................... 10-2023-0054323

(51) Int. Cl.
*A61B 8/08* (2006.01)
*A61B 8/00* (2006.01)

(52) U.S. Cl.
CPC .............. *A61B 8/085* (2013.01); *A61B 8/463* (2013.01); *A61B 8/464* (2013.01); *A61B 8/469* (2013.01); *A61B 8/481* (2013.01)

(58) Field of Classification Search
CPC ......... A61B 8/085; A61B 8/463; A61B 8/464; A61B 8/469; A61B 8/481; A61B 8/5207;
(Continued)

(56) References Cited

U.S. PATENT DOCUMENTS 6,718,055 B1 * 4/2004 Suri ........................ G06T 7/207
600/358
9,398,857 B2 * 7/2016 Choi ...................... A61B 8/469
(Continued)

FOREIGN PATENT DOCUMENTS

CN 105067432 A 11/2015
CN 106485706 A 3/2017
(Continued)

OTHER PUBLICATIONS

VueBox® Quantification Toolbox, Instructions for Use, Bracco Suisse SA (2018) (Year: 2018).*
(Continued)

*Primary Examiner* — Anne M Kozak
*Assistant Examiner* — Jason P Gross
(74) *Attorney, Agent, or Firm* — Morgan Lewis & Bockius LLP

(57) ABSTRACT

An ultrasound imaging disclosure according to an embodiment of the present disclosure relates to an ultrasound imaging apparatus configured to irradiate ultrasonic waves to an object to which an ultrasonic contrast agent is administered, receive an echo signal reflected from the object, and analyze a contrast enhanced ultrasound image for the object, the ultrasound imaging apparatus including an image processor configured to set a region of interest in the ultrasound image, and generate a time intensity curve representing brightness of each frame of the ultrasound image within the set region of interest and a curve fitting model representing a tendency of the time intensity curve according to a predetermined mathematical model.

16 Claims, 14 Drawing Sheets

(58) Field of Classification Search

CPC ......... A61B 8/5223; A61B 8/06; A61B 6/481; A61B 6/504; A61B 8/0891; A61B 8/5246; A61B 5/4244; A61B 6/461; A61B 6/486; A61B 8/461; G06T 2207/10132; G06T 7/0016; G06T 2207/30056; G06T 2200/24; G06T 2207/10024; G06T 2207/10096; G06T 2207/30104; A61M 5/007; A61M 2205/502

See application file for complete search history.

(56) References Cited

U.S. PATENT DOCUMENTS

| | | | |
|---|---|---|---|
| 9,795,352 B2 | 10/2017 | Sakaguchi et al. | |
| 10,032,268 B2 | 7/2018 | Carmi | |
| 10,130,342 B2 * | 11/2018 | Frinking | A61B 8/5223 |
| 2009/0028406 A1 * | 1/2009 | Arditi | A61B 8/13 |
| | | | 382/131 |
| 2010/0060644 A1 * | 3/2010 | Elie | A61B 8/06 |
| | | | 703/2 |
| 2011/0015522 A1 * | 1/2011 | Arditi | A61B 8/481 |
| | | | 600/431 |
| 2015/0221082 A1 * | 8/2015 | Carmi | A61B 8/5223 |
| | | | 382/128 |
| 2018/0185010 A1 * | 7/2018 | Gu | A61B 8/481 |
| 2019/0015074 A1 * | 1/2019 | Gu | A61B 8/085 |
| 2020/0146751 A1 * | 5/2020 | Higaki | A61M 5/145 |
| 2021/0000448 A1 * | 1/2021 | Rychak | A61B 8/0883 |
| 2022/0414972 A1 * | 12/2022 | Rohrer | A61B 5/055 |
| 2023/0225709 A1 * | 7/2023 | Yoshiara | G06T 7/0012 |
| | | | 600/458 |
| 2023/0346330 A1 * | 11/2023 | So | A61B 5/026 |

FOREIGN PATENT DOCUMENTS

| | | |
|---|---|---|
| CN | 113077439 A | 7/2021 |
| JP | 5361410 B2 | 9/2013 |
| JP | 2017-108824 A | 6/2017 |
| JP | 7053910 B1 | 4/2022 |
| KR | 10-1025490 B1 | 4/2011 |
| KR | 10-2241374 B1 | 4/2021 |
| KR | 10-2272741 B1 | 6/2021 |
| WO | 2004/110279 A1 | 12/2004 |
| WO | 2014/096863 A1 | 6/2014 |

OTHER PUBLICATIONS

Chen et al, Imaging features of hepatocellular carcinoma in the non-cirrhotic liver with sonazoid-enhanced contrast-enhanced ultrasound. Diagnostics. Sep. 20, 2022;12(10):2272. (Year: 2022).*

European Office Action dated Jul. 24, 2024 issued in European Patent Application No. 23184021.6.

Office Action dated Mar. 27, 2025 issued in corresponding European Patent Application No. 23184021.6. (Note: US 2015/221082 A1 and Barr Richard G et al. already submitted.).

Yo-Jin Kang et al., "The Principle of Contrast-enhanced Ultrasound and the Diagnosis of Hepatocellular Carcinoma," Korean Journal of Abdominal Radiology, vol. 6(1), No. 12-21, Jul. 15, 2022, URL: https://doi.org/10.52668/kjar.2022.00129.

Richard G. Barr et al., "Contrast-enhanced ultrasound imaging of the liver: a review of the clinical evidence for SonoVue and Sonazoid," Abdominal Radiology, vol. 45, pp. 3779-3788, May 18, 2020, URL: https://doi.org/10.1007/s00261-020-02573-9.

Yasunori Minami et al., "Contrast-enhanced harmonic ultrasound imaging in ablation therapy for primary hepatocellular carcinoma," World J Radiol., Dec. 31, 2009, vol. 1(1), pp. 86-91, Dec. 31, 2009, URL: https://www.ncbi.nlm.nih.gov/pmc/articles/PMC2999306.

Hak Jong Lee et al., "The Application of Contrast Enhanced Ultrasound in Molecular Imaging," Journal of Korean Society of Ultrasound in Medicine, vol. 28(3), pp. 139-145, Sep. 1, 2009.

Press Release_Sonazoid Release_GE HealthCare (Korea), May 11, 2012.

Lognormal Distribution, Wikipedia.

Normal Distribution, Encyclopedia of Mechanical Engineering, URL: https://100.daum.net/encyclopedia/ view/156XX58611433.

Log Normal Distribution, Log Normal Distribution, Information and communication technology glossary, Feb. 13, 2022.

Fergadi, et al., "A meta-analysis evaluating contrast-enhanced intraoperative ultrasound (CE-IOUS) in the context of surgery for colorectal liver metastases", 2021, Abdominal Radiology, vol. 46, p. 4178-4188, XP 037532384, https://doi.org/10.1007/s00261-021-03096-7.

Extended European Search Report issued Nov. 8, 2023 for European Patent Application No. 23184021.6.

Communication pursuant to Article 94(3) EPC dated Aug. 11, 2025 issued in the corresponding European Patent Application No. 23184021. 6. (Note: US 2015/221082 A1, and Barr Richard G et al. previously cited.).

Communication under Rule 71(3) EPC dated Jan. 29, 2026 issued in the corresponding European U.S. Appl. No. 10/032,268. (Note: U.S. Appl. No. 10/032,268B2, and US 2015/221082 A1 previously cited.).

\* cited by examiner

FIG. 2

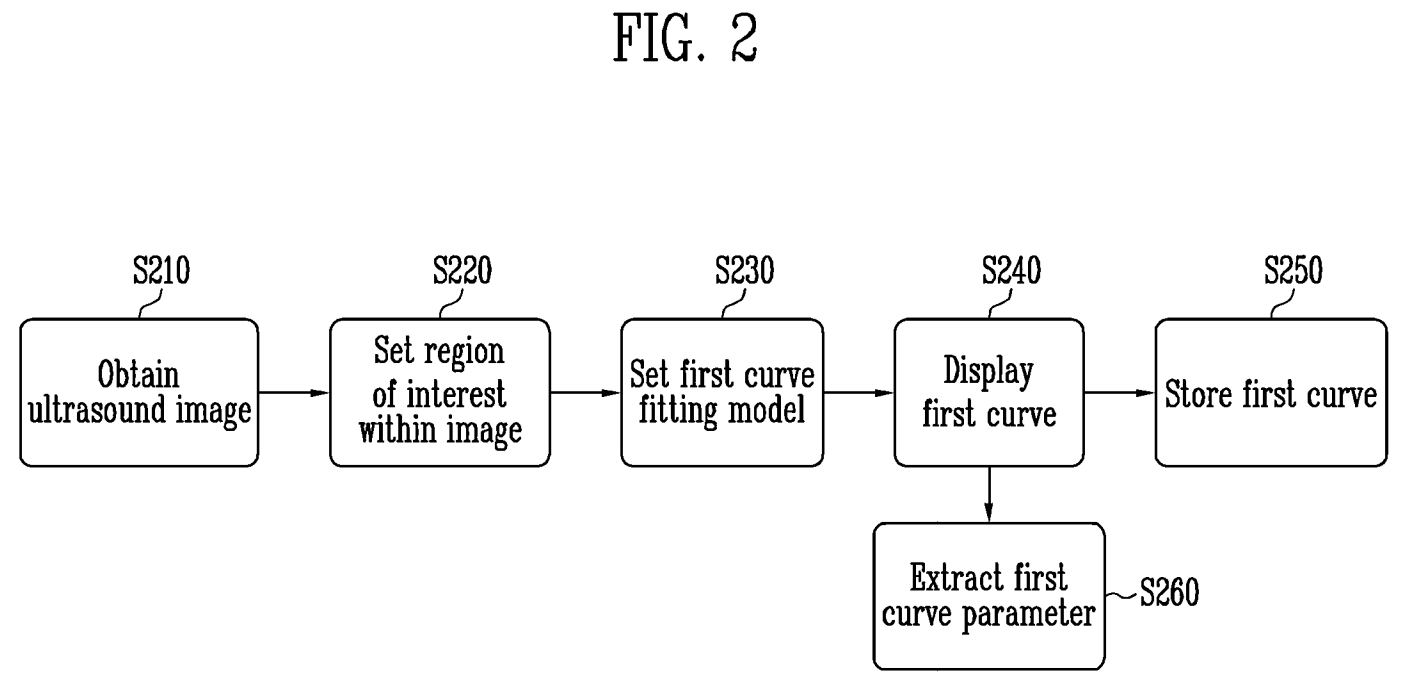

S210 — Obtain ultrasound image

S220 — Set region of interest within image

S230 — Set first curve fitting model

S240 — Display first curve

S250 — Store first curve

S260 — Extract first curve parameter

<u>140</u>

ULTRASOUND IMAGING APPARATUS FOR DISPLAYING A KUPFFER PHASE BASED ON CONTRAST-ENHANCED IMAGES

CROSS-REFERENCE TO RELATED APPLICATION

The present application claims priority under 35 U.S.C. § 119(a) to Korean patent application number 10-2023-0009720 filed on Jan. 25, 2023 and Korean patent application number 10-2023-0054323 filed on Apr. 25, 2023, in the Korean Intellectual Property Office, the entire disclosure of which is incorporated by reference herein.

BACKGROUND

1. Technical Field

The present disclosure relates to an ultrasound imaging apparatus and an operating method thereof.

2. Related Art

Ultrasound imaging refers to imaging sound waves that are reflected from the inside after sending high-frequency sound waves from a surface of the human body to the inside of the body, and ultrasound images can be provided in real time through ultrasound examination. The ultrasonic imaging apparatus has changed from the conventional analog method to the digital method, has changed from a 2D ultrasound imaging apparatus to a 3D ultrasound imaging apparatus, and to a 4D ultrasound imaging apparatus that includes the passage of time, and recently, a 4D ultrasound apparatus that even expresses the movement of a 3D image is being developed.

An ultrasound imaging apparatus is an apparatus that irradiates an ultrasound signal generated from a transducer of a probe to an object, receives information of an echo signal reflected from the object, and obtains an image of a part inside the object, and such an ultrasound imaging apparatus is more stable than imaging apparatuses using X-rays and has the advantage of being able to display images in real time, and thus is widely used together with other imaging diagnosis apparatuses. In particular, ultrasound imaging apparatuses are widely used in various diagnostic processes because they are more accurate than other diagnostic apparatuses and safe because there is no risk of radiation exposure to the human body.

As an ultrasound imaging method, there is a contrast enhanced ultrasound (CEUS) examination method. A contrast agent is a microparticle or microbubble that can be detected by an imaging apparatus, and the contrast agent can be easily detected in a process of receiving a reflected echo signal. Accordingly, the contrast enhanced ultrasound examination method can increase the resolution of an ultrasound image and make internal organs appear clearly.

The contrast enhanced ultrasound examination method may be used to observe a tendency of an echo signal value reflected from an object over time. To this end, a time intensity curve (TIC) representing an echo signal for each frame of an ultrasound image may be created. A user may observe a tendency of the echo signal value based on the time intensity curve and analyze a change in contrast agent concentration over time. The user may diagnose a lesion of the object through the time intensity curve or the change in contrast agent concentration. In particular, the user may quantitatively determine whether a tumor of the object is malignant through the time intensity curve or the change in contrast agent concentration.

However, the response characteristics (brightness change over time) to the contrast agent differ depending on the presence or absence of lesions and the type of contrast agent. Therefore, in order to identify a specific lesion of an object, it is necessary to specify a contrast agent and to quantify the object's response to the contrast agent.

SUMMARY

An object of the present disclosure is to provide an ultrasound imaging apparatus and an operating method thereof, which provide objective diagnosis results for lesions by specifying a contrast agent, quantifying and modeling response characteristics to the contrast agent.

Tasks of the present disclosure are not limited to the tasks mentioned above, and other tasks not mentioned will be clearly understood by those skilled in the art from the description below.

In accordance with an aspect of the present disclosure, there is provided an ultrasound imaging apparatus configured to irradiate ultrasonic waves to an object to which an ultrasonic contrast agent is administered, receive an echo signal reflected from the object, and analyze a contrast enhanced ultrasound image for the object, the ultrasound imaging apparatus including an image processor configured to set a region of interest in the ultrasound image, and generate a time intensity curve representing brightness of each frame of the ultrasound image within the set region of interest and a curve fitting model representing a tendency of the time intensity curve according to a predetermined mathematical model, wherein the image processor is configured to generate a first curve based on a first time intensity curve obtained from an object to which a first contrast agent is administered, generate a second curve based on a second time intensity curve obtained from an object to which a second contrast agent is administered, and generate a third curve through a difference operation of parameter values of the first curve and the second curve.

Specifically, the first curve may include a bell-shaped curve, and the second curve may include a bell-shaped curve or a periodic function-shaped curve.

Specifically, the image processor may be configured to perform the difference operation, after the first curve and the second curve are normalized or time-synchronized. Specifically, the ultrasound imaging apparatus may further include a display unit configured to display any one or more of the ultrasound image, the first curve, the second curve, and the third curve, and the display unit may be configured to display any one or more of a first curve button indicating that the first curve is stored in a storage, a second curve button indicating that the second curve is stored in the storage, and a difference operation button controlling a performance of the difference operation.

Specifically, the display unit may include a first display unit and a second display unit, wherein the first display unit may be configured to display any one or more of the ultrasound image, the first curve, the second curve, and the third curve, and the second display unit may be configured to display any one or more of the first curve button, the second curve button, and the difference operation button.

Specifically, the second display unit may be a touch screen on which information is input by a user's touch, wherein when the first curve button is touched, the first curve may be displayed, when the second curve button is touched, the second curve may be displayed, and when the second curve button is displayed or the difference operation button is touched, the difference operation may be performed.

Specifically, the parameter value may be any one or more of PI (Peak Intensity), TTP (Time to Peak), WiR (Wash in Rate: Max. Slope), WoR (Wash out Rate: Min. Slope), T1 (time of intersection of x-axis of WiR), T2 (time of intersection of x-axis of WoR), RT (Rise Time), FT (Falling Time), iAUC (Wash in Area Under the Curve), oAUC (Wash out Area Under the Curve), AUC (Area Under the Curve), and MTT (Mean Transit Time), and the image processor may be configured to determine whether a result of the difference operation is equal to or less than a predetermined value.

In accordance with another aspect of the present disclosure, there is provided an ultrasound imaging apparatus configured to irradiate ultrasonic waves to an object to which an ultrasonic contrast agent is administered, receive an echo signal reflected from the object, and analyze a contrast enhanced ultrasound image for the object, the ultrasound imaging apparatus including an image processor configured to set a region of interest in the ultrasound image, and generate a time intensity curve representing brightness of each frame of the ultrasound image within the set region of interest and a curve fitting model representing a tendency of the time intensity curve according to a predetermined mathematical model, wherein the image processor is configured to generate a second curve based on a second time intensity curve obtained from an object to which a second contrast agent is administered, and the second contrast agent is a Sonazoid contrast agent.

Specifically, the ultrasound imaging apparatus may further include a display unit configured to display any one or more of a first function graph displaying a first function representing a vascular phase as a graph, a second function graph displaying a second function representing a Kupffer phase as a graph, and the second curve.

In accordance with another aspect of the present disclosure, there is provided an operating method of an ultrasound imaging apparatus configured to irradiate ultrasonic waves to an object to which an ultrasonic contrast agent is administered, receive an echo signal reflected from the object, and analyze a contrast enhanced ultrasound image for the object, the operating method including: setting a region of interest in the ultrasound image; obtaining a time intensity curve representing brightness of each frame of the ultrasound image within the region of interest and a curve fitting model representing a tendency of the time intensity curve according to a predetermined mathematical model; generating a first curve based on a first time intensity curve obtained from an object to which a first contrast agent is administered; generating a second curve based on a second time intensity curve obtained from an object to which a second contrast agent is administered; and generating a third curve through a difference operation of parameter values of the first curve and the second curve.

Specifically, the first curve may include a bell-shaped curve, and the second curve may include a bell-shaped curve or a periodic function-shaped curve.

Specifically, after the first curve and the second curve are normalized or time-synchronized, the difference operation may be performed.

Specifically, the operating method may further include displaying any one or more of the ultrasound image, the first curve, the second curve, and the third curve, and displaying any one or more of a first curve button indicating that the first curve is stored in a storage, a second curve button indicating that the second curve is stored in the storage, and a difference operation button controlling a performance of the difference operation.

Specifically, any one or more of the ultrasound image, the first curve, the second curve, and the third curve may be displayed on a first display unit, and any one or more of the first curve button, the second curve button, and the difference operation button may be displayed on a second display unit.

Specifically, the second display unit may be a touch screen on which information is input by a user's touch, wherein when the first curve button is touched, the first curve may be displayed, when the second curve button is touched, the second curve may be displayed, and when the second curve button is displayed or the difference operation button is touched, the difference operation may be performed.

Specifically, the parameter value may be any one or more of PI (Peak Intensity), TTP (Time to Peak), WiR (Wash in Rate: Max. Slope), WoR (Wash out Rate: Min. Slope), T1 (time of intersection of x-axis of WiR), T2 (time of intersection of x-axis of WoR), RT (Rise Time), FT (Falling Time), iAUC (Wash in Area Under the Curve), oAUC (Wash out Area Under the Curve), AUC (Area Under the Curve), and MTT (Mean Transit Time), and the operating method may further include determining whether a result of the difference operation is equal to or less than a predetermined value.

According to an ultrasound imaging apparatus and an operating method thereof in accordance with the present disclosure, it is possible to provide a user with basic information for diagnosing a tumor based on a time intensity curve for a contrast agent.

The effects of the present disclosure are not limited to the above-described effects, and effects not mentioned will be clearly understood by those skilled in the art from the present specification and the accompanying drawings.

BRIEF DESCRIPTION OF THE DRAWINGS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the drawing figures, dimensions may be exaggerated for clarity of illustration. It will be understood that when an element is referred to as being "between" two elements, it can be the only element between the two elements, or one or more intervening elements may also be present. Like reference numerals refer to like elements throughout.

FIG. 2 is a flowchart illustrating an operating method of an ultrasound imaging apparatus in accordance with a first embodiment of the present disclosure.

DETAILED DESCRIPTION

Figure 1:
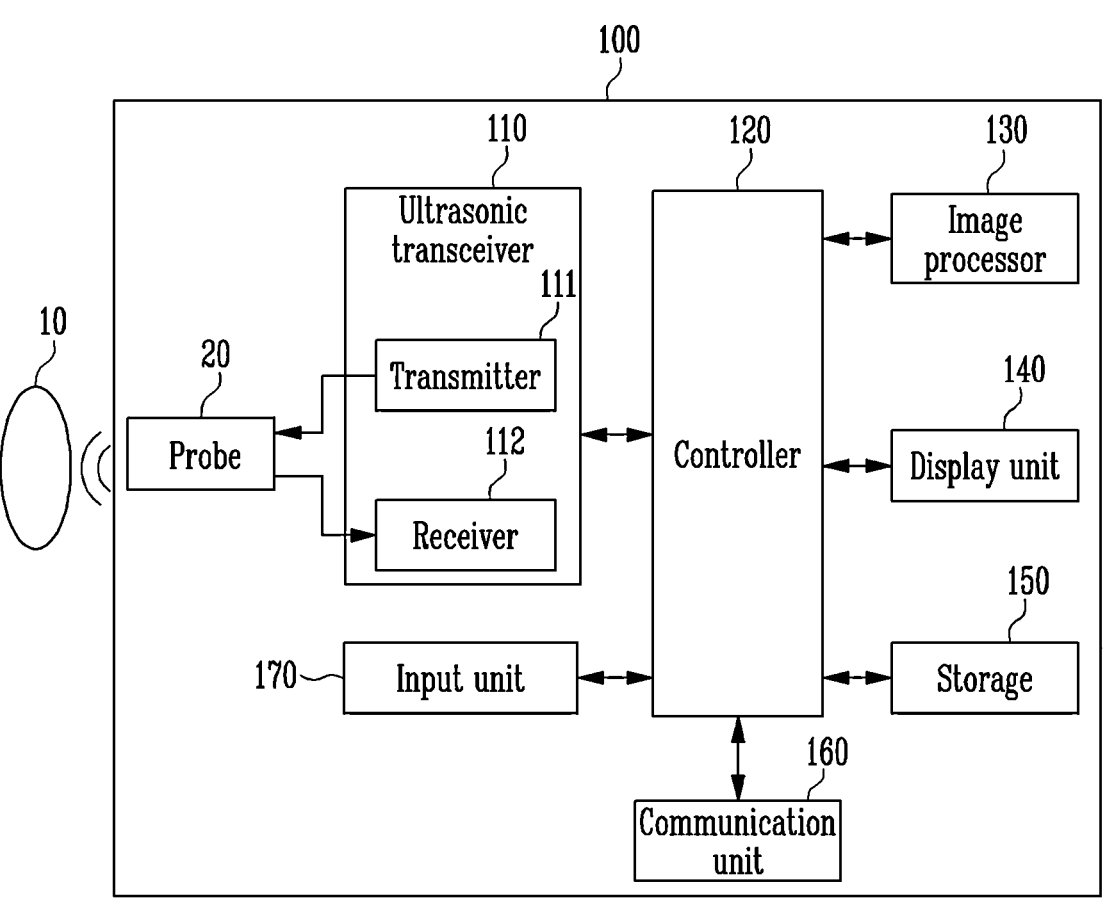
FIG. 1 is a block diagram illustrating a configuration of an ultrasound imaging apparatus 100 in accordance with an embodiment of the present disclosure.

The present specification clarifies the scope of the present disclosure and, to enable those of ordinary skill in the art to which the present disclosure pertains to practice the present disclosure, the principle of the present disclosure is explained and embodiments are disclosed. The disclosed embodiments may be implemented in various forms.

Throughout the specification, when a part is "connected" to another part, it includes not only a case of being directly connected but also a case of being indirectly connected, and the indirect connection includes connection through a wireless communication network.

In addition, terms used herein are used to describe the embodiments, not intended to limit and/or restrict the disclosed invention. The singular expression includes the plural expression unless the context clearly dictates otherwise. In the present specification, terms such as "comprise" or "have" specify the presence of stated features, integers, steps, operations, elements, components or a combination thereof, but do not preclude the presence or addition of one or more other features, integers, steps, operations, elements, components, a combination thereof.

Further, although terms including ordinal numbers such as "first," "second," and the like are used to explain various components, the components are not limited to such terms and these terms are used only to distinguish one component from another component. For example, a first component may be referred to as a second component, or similarly, the second component may be referred to as the first component within the scope of the present disclosure.

In addition, terms used herein such as "first," "second," or "first-1" are exemplary terms for referring to different components, entities, images, pixels, or patches. Therefore, the terms such as "first", "second" or "first-1" do not indicate an order or priority among components.

In addition, terms such as "unit", "group", "block", "member", and "module" may refer to a unit that processes at least one function or operation. For example, the terms may refer to at least one process processed by at least one hardware such as a field-programmable gate array (FPGA)/application specific integrated circuit (ASIC), at least one software stored in a memory, or a processor.

Symbols given to each step are used to identify each step, and these signs do not indicate the order between the steps, and each step may be performed differently from the stated order unless the context clearly indicates a specific order.

In addition, an image herein may include a medical image acquired by a medical imaging apparatus such as a magnetic resonance imaging (MRI) apparatus, a computed tomography (CT) apparatus, an ultrasound imaging apparatus, or an X-ray imaging apparatus, and ultrasound images and medical images of other modalities other than ultrasound may be provided or controlled.

Further, the term 'object' as used herein refers to a subject to be photographed, and may include human, animal, or a part thereof. For example, the object may include a part of the body (such as organs) or a phantom.

Throughout the specification, the term "ultrasound image" as used herein refers to an image for an object transmitted to the object and processed based on an ultrasound signal reflected from the object.

Hereinafter, an embodiment according to the present disclosure will be described in detail with reference to the accompanying drawings.

FIG. 1 is a block diagram illustrating a configuration of an ultrasound imaging apparatus 100 in accordance with any one embodiment of the present disclosure.

The ultrasound imaging apparatus 100 according to an embodiment of the present disclosure may include a probe 20, an ultrasonic transceiver 110, a controller 120, an image processor 130, a display unit 140, a storage 150, a communication unit 160, and an input unit 170.

The ultrasound imaging apparatus 100 may be provided not only as a cart type but also as a portable type. Examples of the portable ultrasound imaging apparatus may include a smart phone, a laptop computer, a PDA, and a tablet PC including a probe and an application, but are not limited thereto.

The probe 20 may include a plurality of transducers. The plurality of transducers may transmit an ultrasound signal to an object 10 according to a transmission signal applied from a transmitter 111. The plurality of transducers may be configured to receive the ultrasound signal reflected from the object 10 to generate a received signal. In addition, the probe 20 may be integrated with the ultrasound imaging apparatus 100 or may be provided as a separate type connected to the ultrasound imaging apparatus 100 by a wire or wirelessly. Moreover, the ultrasound imaging apparatus 100 may include one or a plurality of probes 20 according to an implementation form.

The controller 120 is configured to control, in consideration of the position and focal point of the plurality of transducers included in the probe 20, the transmitter 111 to generate a transmission signal to be applied to each of the plurality of transducers.

The controller 120 is configured to convert the received signal received from the probe 20 from analog to digital and, in consideration of the positions and focal points of the plurality of transducers, add the digitally converted received signals to control the receiver 112 to generate ultrasound data.

The image processor 130 is configured to generate an ultrasound image by using the ultrasound data generated by the ultrasound receiver 112.

Meanwhile, the ultrasound image may represent the motion of the object as a Doppler image as well as a gray scale ultrasound image obtained by scanning the object according to the A mode (amplitude mode), the B mode (brightness mode), and the M mode (motion mode).

A-mode is the most basic form of ultrasound image display method, which is a method that displays the intensity of the reflected sound as the amplitude size on the time (distance) axis, and if the reflected sound is strong, the amplitude is high, and if the reflected sound is weak, the amplitude is low, which is advantageous for distance measurement, but this mode is rarely used at present because the image changes even if the direction of the probe is slightly changed.

M-mode is a mode in which the distance of the moving reflector is displayed as a temporal change in the changed form of A-mode. By specifying the region of interest (ROI) in the 2D image as an M line and displaying the change over time in that area, it is mainly used to observe heart valves, and may also record fetal heart sounds, but has recently been replaced by the Doppler method.

B-mode is a method of displaying the reflected sound as the brightness of a dot, which is currently used in most ultrasound diagnostic equipment, and the brightness of each dot is proportional to the amplitude of the reflected signal, and recently provides a brightness level of 256 or more, and is also a mode in which long-term motions are visualized and displayed as they are in real time. The mode called 2D mode, which means B (brightness) mode, displays the cross-sectional image of an object in real time on the screen in black and white shades, and is the most used mode.

In addition, the Doppler mode is a mode that measures blood flow by detecting the flow of red blood cells in blood vessels in general, which uses the principle that the wavelength shortens when red blood cells approach the probe and lengthens when they move away, and there are color Doppler, pulse wave Doppler (PW), continuous wave Doppler (CW), etc., according to the method of displaying blood flow. The Doppler image may include a blood flow Doppler image showing blood flow (also called color Doppler image), a tissue Doppler image showing tissue movement and a spectral Doppler image displaying the moving speed of the object in a waveform.

In addition, as a composite mode, there are a mode in which two or three modes are simultaneously applied to one image to display other modes based on 2D, and a 3D mode in which a 3D stereoscopic image is displayed.

In the B-mode processing process, B-mode components are extracted and processed from ultrasound data, and in the image generation process, an ultrasound image in which signal intensity is expressed as brightness may be generated based on the B mode component extracted in the B mode processing process. In the Doppler processing process, Doppler components are extracted from ultrasound data, and in the image generation process, a Doppler image expressing the motion of the object in color or waveform may be generated based on the extracted Doppler component.

In the image generation process, a 2D ultrasound image or a 3D image of the object may be generated, and an elastic image obtained by imaging the degree of deformation of the object according to pressure may also be generated. Furthermore, various types of additional information may be expressed as text or graphics on the ultrasound image. Meanwhile, the generated ultrasound image may be stored in a memory.

In the process of measuring the object in the ultrasound image, a measurement tool for measuring the object may be determined, and one of a plurality of measurement tools may be selected based on a user input.

For example, a measurement tool selection menu for selecting one of the plurality of measurement tools may be provided, and the measurement tool selection menu may be displayed on one screen together with the ultrasound image. In addition, the measurement tool selection menu may be displayed on a separate screen different from the touch screen on which the ultrasound image is displayed.

In addition, one of the plurality of measurement tools may be determined based on a user input for selecting one of the plurality of measurement items to be measured. The measurement item may include, but is not limited to, length, width, or angle.

As a user input for selecting one of the measurement items is received, a predetermined measurement tool may be determined corresponding to the selected measurement item.

The image processor 130 may generate a time intensity curve representing image signal values for each frame of the ultrasound image within the set region of interest. Specifically, the image processor 130 may extract and digitizes image signal values of pixels of the region of interest in the ultrasound image, for example, a brightness value of each pixel in the region of interest, and calculate the total and average values of brightness values of each pixel for each ultrasound image frame. The image processor 130 may generate a graph showing the calculated average value of brightness of pixels in the region of interest with respect to frames of the ultrasound image, and generate a time intensity curve (TIC) based on this. The time intensity curve is mainly used in ultrasound examination using an ultrasound contrast agent. A graph may be created using not only the average value of brightness, but also the sum, the median, the maximum value, the minimum value, and the like, and based on this, a time intensity curve may be generated.

Errors may occur, such as the probe not being able to contact the object, the object leaving the region of interest, or the size of the region of interest changing, and such errors introduce glitches in the readout based on the time intensity curve. In the case that it is determined that the above error has occurred, the time intensity curve may be obtained again.

The image processor 130 may analyze the tendency of the time intensity curve based on a predefined mathematical model, and generate a graph of values according to the analyzed tendency for frames of the ultrasound image. In an embodiment, the predefined mathematical model may include at least one of a Polynomial, Exponential rise, Gamma variant, and a Gompertz model. The image processor 130 may generate a fitting curve representing the tendency of the time intensity curve based on a user input for selecting at least one of the Polynomial, Exponential rise, Gamma variant, and Gompertz model. However, it is not limited thereto, and the image processor 130 may generate a fitting curve based on a predetermined mathematical model among the mathematical models listed above. Since a technique of generating a fitting curve representing the tendency of the time intensity curve based on at least one of the Polynomial, Exponential rise, Gamma variant and Gompertz model is a technique known to those skilled in the art, a detailed description thereof will be omitted.

The display unit 140 may be configured to display the generated ultrasound image and various information processed in the ultrasound imaging apparatus 100. The ultrasound imaging apparatus 100 may include one or a plurality of display units 140 according to an implementation form. In addition, the display unit 140 may be provided as a touch screen in combination with a touch panel.

The controller 120 may control the overall operation of the ultrasound imaging apparatus 100 and a signal flow between internal components of the ultrasound imaging apparatus 100. The controller 120 may include a memory configured to store a program or data for performing a function of the ultrasound imaging apparatus 100, and a processor configured to process a program or data. In addition, the controller 120 may be configured to receive a control signal from the input unit 170 or an external device to control the operation of the ultrasound imaging apparatus 100.

The ultrasound imaging apparatus 100 may include the communication unit 160 and be connected with an external device (e.g., a server, a medical device, a portable device (smartphones, tablet PCs, wearable devices, etc.)) through the communication unit 160.

The communication unit 160 may include one or more components that enable communication with the external device, including, for example, at least one of short-range communication modules, wired communication modules, and wireless communication modules.

It is also possible that the communication unit 160 receives a control signal and data from the external device and transmits the received control signal to the controller 120 so as to have the controller 120 control the ultrasound imaging apparatus 100 according to the received control signal.

Alternatively, it is also possible that the controller 120 transmits a control signal to the external device through the communication unit 160 to control the external device in accordance with the control signal of the controller.

For example, the external device may be configured to process data of the external device in accordance with the control signal of the controller received through the communication unit.

A program (such as artificial intelligence) capable of controlling the ultrasound imaging apparatus 100 may be installed in the external device, such that the program may include instructions for performing some or all of the operations of the controller 120.

The program may be preinstalled in the external device or may be installed by downloading, by a user of the external device, the program from a server that provides an application. The server providing the application may include a recording medium in which the corresponding program is stored.

In addition, the program may include a storage medium of a server or a storage medium of a client device in a system consisting of a server and a client device. Alternatively, if there is a third device (smartphones, tablet PCs, wearable devices, etc.) that is communicatively connected to the server or client device, the program product may include a storage medium of the third device. Alternatively, the program may include a S/W program itself transmitted from the server to the client device or the third device, or transmitted from the third device to the client device.

In this case, one of the server, the client device, and the third device may execute the program to perform methods according to the disclosed embodiments. Alternatively, two or more of the server, the client device, and the third device may execute the program to perform the methods according to the disclosed embodiments by distributing the methods.

For example, a server (e.g., a cloud server or an artificial intelligence server, etc.) may execute a program stored in the server, so as to control the client device that is communicatively connected to the server to perform the method according to the disclosed embodiments.

An operating method of an ultrasound imaging apparatus according to an embodiment may be implemented in the form of program instructions that can be executed by various computer means and recorded in a computer-readable medium. The computer-readable medium may include program instructions, data files, data structures, and the like, alone or in combination. Program instructions recorded on the medium may be those specifically designed and configured for the present disclosure or may be known and available to those skilled in the computer software art. Examples of computer-readable recording media include magnetic media such as hard disks, floppy disks, and magnetic tapes, optical media such as CD-ROMs and DVDs, magneto-optical media such as floptical disks, and hardware devices specifically configured to store and execute program instructions such as ROM, RAM, flash memory, and the like. Examples of program instructions include machine code, such as those generated by compilers, as well as high-level language code that can be executed by a computer using an interpreter or the like.

In addition, the ultrasound imaging apparatus and the operating method of the ultrasound imaging apparatus according to the disclosed embodiments may be included in the computer program product and provided. Computer program products may be traded between sellers and buyers as commodities.

The computer program product may include an S/W program or a storage medium readable by a computer in which the S/W program is stored. For example, a computer program product may include a product in the form of an S/W program (e.g., a downloadable app) electronically distributed through a manufacturer of an electronic device or an electronic market (e.g., Google Play Store, App Store). For electronic distribution, at least a portion of the S/W program may be stored on a storage medium or temporarily generated. In this case, the storage medium may be a storage medium of a manufacturer's server, an electronic market server, or a relay server temporarily storing SW programs.

The storage 150 may be configured to store various data or programs for driving and controlling the ultrasound imaging apparatus 100, input/output ultrasound data, and an acquired ultrasound image.

The input unit 170 may be configured to receive a user input for controlling the ultrasound imaging apparatus 100. For example, the user input may include an input for manipulating a button, a keypad, a mouse, a trackball, a jog switch, a knob, etc., an input for touching a touch pad or a touch screen, a voice input, a motion input, and an input of biometric information (e.g., iris recognition, fingerprint recognition, etc.), but is not limited thereto.

The block diagram of the ultrasound imaging apparatus 100 shown in FIG. 1 is a block diagram for an embodiment, and each component of the block diagram of FIG. 1 may be integrated, added, or omitted according to specifications of the ultrasound imaging apparatus 100 that is actually implemented. In other words, if necessary, two or more components may be combined into one component, or one component may be subdivided into two or more components. In addition, the functions performed in each block are for explaining the embodiments, and the specific operation or device does not limit the scope of the present disclosure.

FIG. 2 is a flowchart illustrating an operating method of an ultrasound imaging apparatus in accordance with a first embodiment of the present disclosure.

In operation S210, the image processor 130 may generate an ultrasound image using information of the echo signal received from the object using the probe 20. After the ultrasound contrast agent containing microbubbles is injected into the object by intravenous injection, the echo signal may be received from the object 10 using the probe 20, and at this time, the ultrasound imaging apparatus 100 may obtain contrast enhanced mode data.

The image processor 130 may process ultrasound image data according to the image display mode. The image processor 130 may obtain B-mode data (brightness mode data) or contrast enhanced mode data by performing processes such as amplification, logarithmic compression, and envelope detection on the echo signal from the ultrasonic transceiver, and the image processor 130 may generate an ultrasound image using data. The storage 150 may store the image generated by the image processor 130.

The image processor 130 may generate one or more ultrasound images and may integrate one or more ultrasound images into one. In the process of integrating the ultrasound image, some sections of the ultrasound image may be interpolated.

The image processor 130 may use a strong nonlinear effect of the ultrasound contrast agent in the contrast enhanced mode. The nonlinear effect is that the reflected wave from the microbubbles is greatly distorted compared to the incident wave, and harmonic components are generated when the waveform is distorted, and the image processor 130 may use a contrast harmonic imaging method that suppresses the fundamental wave and further emphasizes the contrast agent by imaging a second harmonic of the irradiation wave using a nonlinear effect. In the contrast harmonic imaging method, since the reflected wave from bubbles contains more second harmonics than the reflected wave from living tissue, an image in which the reflected wave from the contrast agent is emphasized is obtained.

In operation S220, the input unit 170 may receive a user input for selecting an area of interest included in the object 10. The image processor 130 may display an image representing the region of interest generated based on the user input, and the region of interest may be indicated as a region of interest by a specific display. However, it is not limited thereto, and the image processor 130 may automatically set a region of interest where a specific lesion is located in the object. For example, the image processor 130 may recognize a tumor region and automatically set a region of interest along the periphery of the tumor.

In operation S230, the image processor 130 may set a curve fitting model according to the contrast agent injected into the object 10. The curve fitting model may be a mathematical model function and may be statistically derived from ultrasound data obtained in an ultrasound diagnosis process. The curve fitting model may be a time intensity curve (TIC) representing image signal values for each frame of an ultrasound image within a set region of interest.

Since different contrast agents may have different responses in the object 10, the curve fitting model may vary depending on the contrast agents. For example, ultrasound contrast agents can be classified into pure-vascular agents and Kupffer agents. SonoVue (Bracco), a representative pure-vascular agent, has a diameter similar to that of red blood cells and does not pass through vascular endothelium, so there is no migration of the contrast agent into the interstitial space, resulting in pure vascular phase image. On the other hand, a representative Kupffer agent Sonazoid (GE healthcare), like SonoVue, has a diameter similar to that of red blood cells and does not pass through the vascular endothelium to generate vascular phase images, and at the same time, it is phagocytosed by Kupffer cells, which are macrophages in the liver, and has the characteristic of showing echogenicity that lasts for more than several tens of minutes in the liver parenchyma, so that Kupffer phase images can also be generated.

The curve fitting model of the present disclosure can be modeled by the following equation 1. Equation 1 can be statistically derived from ultrasound data obtained in the ultrasound diagnosis process using the first contrast agent.

$$I_V(t) = \frac{C_1}{\sqrt{2\pi}\,\sigma_1(t-t_0)}e^{\frac{-[\ln(t-t_0)-\mu_1]^2}{2\sigma_1^2}} + C_0, \, t > t_0 \qquad \text{[Equation 1]}$$

The signs of the above equation have the following meanings. $I_V(t)$: Intensity curve of vascular phase, t: Time, $t_0$: Contrast agent injection point (start time), $C_1$: Area under curve of the curve section created based on intensity, $\mu_1$: Mean of the log-normal distribution function, indicating the central position of the distribution, $\sigma_1$: Standard deviation of the log-normal distribution function, indicating the size of the dispersion, $C_0$: Intensity value at $t_0$, used as offset value.

The curve fitting model according to Equation 1 above may express the vascular phase. The curve fitting model may be a log-normal distribution function. Specifically, the curve fitting model according to Equation 1 above has a large distribution near the center and a shape in which the distribution gradually decreases as time t passes, and the shape may represent the characteristics of the vascular phase.

In operation S240, the display unit 140 may display a curve fitting model.

In operation S250, the curve fitting model (first curve) may be stored in the storage 150.

In operation S260, the parameter may be obtained based on the curve fitting model (first curve).

The operations shown in FIG. 2 represent processes of obtaining a first curve (a first curve fitting model), displaying the first curve, and storing the first curve. After obtaining the first curve and storing the first curve according to the operations shown in FIG. 2, as shown in FIG. 3, processes of obtaining a second curve (second curve fitting model), displaying the second curve, and storing the second curve may follow.

One or more contrast agents may be sequentially injected into the object 10, and a curve may be created according to each contrast agent. The first curve obtained in the operations shown in FIG. 2 is obtained by administering the first contrast agent to the object 10, and the second curve obtained in the operations shown in FIG. 3 below is obtained by administering the second contrast agent to the object 10. When one or more contrast agents are injected, the image processor 130 may generate one curve fitting model by combining one or more curve fitting models.

Figure 3:
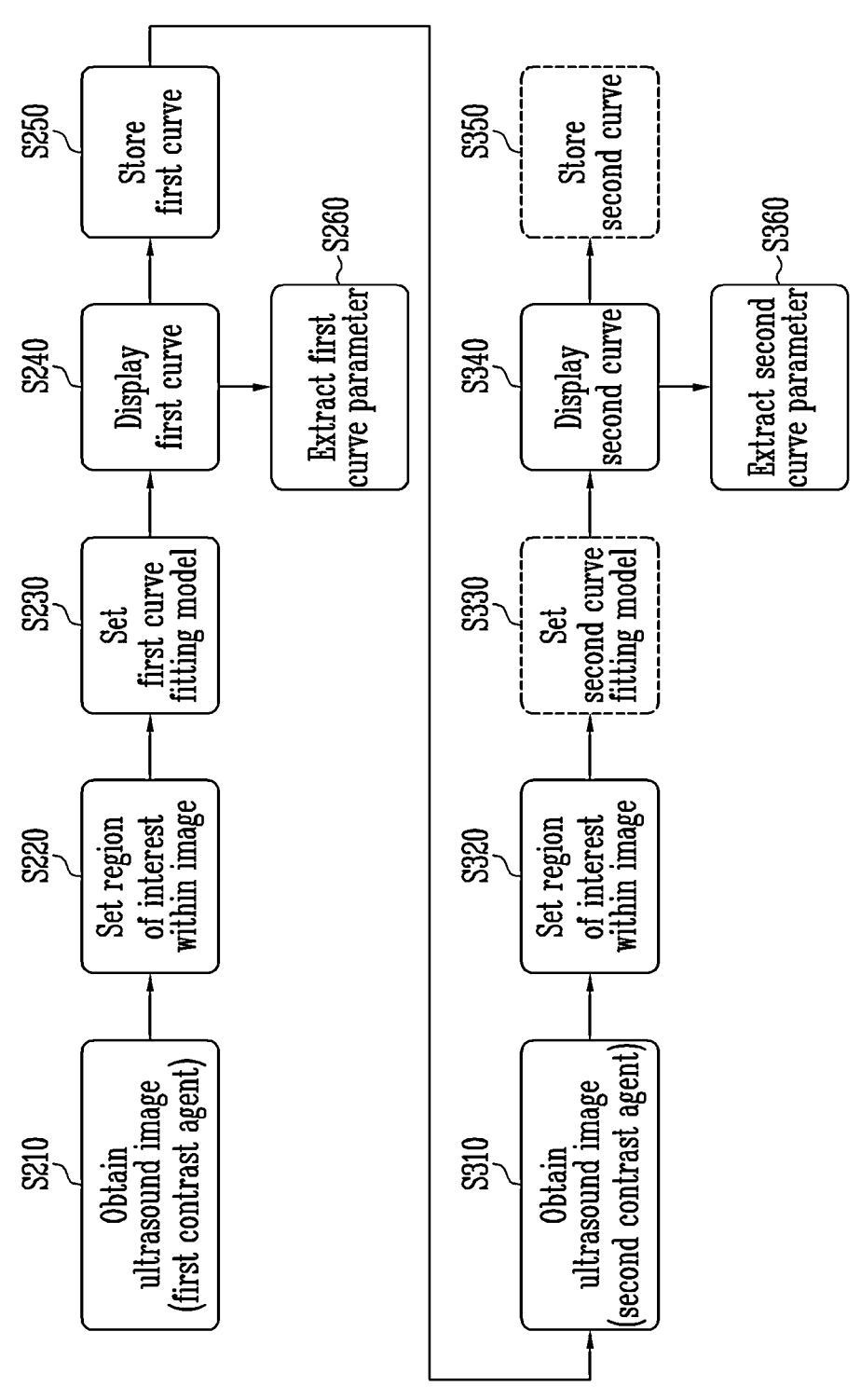
FIG. 3 is a flowchart illustrating an operating method of an ultrasound imaging apparatus in accordance with a second embodiment of the present disclosure.

FIG. 3 is a flowchart illustrating an operating method of an ultrasound imaging apparatus in accordance with a second embodiment of the present disclosure. Descriptions of overlapping contents with those in FIG. 2 may be omitted in FIG. 3.

In operation S310, the image processor 130 may obtain an ultrasound image by receiving information on an echo signal reflected from the object 10. The second contrast agent may be injected into the object 10, and contrast enhanced mode data may be obtained. The second contrast agent may be of a different type from the first contrast agent injected into the object in operation S210. So that the first contrast agent does not affect the second contrast agent image, the second contrast agent may be injected after the first contrast agent is destroyed.

In operation S320, the input unit 170 may receive a user input for selecting a region of interest included in the object 10. The region of interest may include the same region as the region of interest set in operation S220.

In operation S330, the image processor 130 may set a curve fitting model according to the contrast agent injected into the object 10.

The curve fitting model of the present disclosure can be modeled by Equation 2 below. Equation 2 can be statistically derived from ultrasound data obtained in the ultrasound diagnosis process using the second contrast agent.

$$I_K(t) = C_0 + \frac{C_1}{\sqrt{2\pi}\,\sigma_1(t-t_0)}e^{\frac{-[\ln(t-t_0)-\mu_1]^2}{2\sigma_1^2}} + \qquad \text{[Equation 2]}$$

$$\frac{C_2}{\sqrt{2\pi}\,\sigma_2}e^{\frac{-[(t-t_0)-\mu_2]^2}{2\sigma_2^2}}, t > t_0$$

Equation 2 above includes functions 1 and 2 below, first function represents the vascular phase as a log-normal distribution function, and second function represents the Kupffer phase as a normal distribution function.

The signs of Equation 2 above have the following meanings. $I_K(t)$: Intensity curve of vascular phase+Kupffer phase, t: Time, t0: contrast agent injection point (start time), $C_1$: Area under curve of the curve section created based on intensity, $C_2$: Area under curve of the curve section created based on intensity, pi: mean of the log-normal distribution function, indicating the central position of the distribution, $\mu_2$: mean of the normal distribution function, indicating the central position of the distribution, $\sigma_1$: Standard deviation of the log-normal distribution function, indicating the size of the dispersion, $\sigma_2$: Standard deviation of the normal distribution function, indicating the size of the dispersion, $C_0$: Intensity value at to, used as offset value.

$$\frac{C_1}{\sqrt{2\pi}\,\sigma_1(t-t_0)}e^{\frac{-[\ln(t-t_0)-\mu_1]^2}{2\sigma_1^2}}, t > t_0 \qquad \text{[First function]}$$

$$\frac{C_2}{\sqrt{2\pi}\,\sigma_2}e^{\frac{-[(t-t_0)-\mu_2]^2}{2\sigma_2^2}}, t > t_0 \qquad \text{[Second function]}$$

In addition, the curve fitting model of the present disclosure can be modeled by Equation 3 below. Equation 3 can be statistically derived from ultrasound data obtained in the ultrasound diagnosis process using the second contrast agent.

$$I_K(t) = C_0 + \frac{C_1}{\sqrt{2\pi}\,\sigma_1(t-t_0)}e^{\frac{-[\ln(t-t_0)-\mu_1]^2}{2\sigma_1^2}} + C_3\text{Sin}[C_4(t-t_0)], \qquad \text{[Equation 3]}$$

$$t > t_0 \ \ \& \ C_4(t-t_0) \le \frac{\pi}{2}$$

Equation 3 above includes first function and second function below, first function represents the vascular phase as a log-normal distribution function, and second function represents the Kupffer phase as a periodic function.

$$\frac{C_1}{\sqrt{2\pi}\,\sigma_1(t-t_0)}e^{\frac{-[\ln(t-t_0)-\mu_1]^2}{2\sigma_1^2}}, t > t_0 \qquad \text{[First function]}$$

$$C_3\text{Sin}[C_4(t-t_0)], C_4(t-t_0) \le \frac{\pi}{2} \qquad \text{[Second function]}$$

The signs of Equation 3 above have the following meanings. $I_K(t)$: Intensity curve of vascular phase+Kupffer phase, t: Time, t0: Contrast agent injection point (start time), $C_1$: Area under curve of the curve section created based on intensity, $C_3$: amplitude (magnitude) of the periodic function, $C_4$: The angular velocity of the periodic function, which determines the period, $\mu_1$: mean of the log-normal distribution function, indicating the central position of the distribution, $\sigma_1$: Standard deviation of the log-normal distribution function, indicating the size of the dispersion, $C_0$: Intensity value at $t_0$, used as offset value.

As in Equations 2 and 3 above, the curve fitting model according to the present disclosure may be a combination of first function representing the vascular phase and second function representing the Kupffer phase. The curve fitting model according to first function may be a bell-shaped curve or a periodic function curve. In addition, the curve fitting model according to second function may be a bell-shaped curve or a periodic function curve, and accordingly, the curve fitting model according to the present disclosure may be any one of a bell-shaped curve+bell-shaped curve, a bell-shaped curve+periodic function curve, or a periodic function curve+periodic function curve.

For example, curves in the form of a periodic function include Sin function curves and Cos function curves, and bell-shaped curves include curves representing functions such as normal distribution, log-normal distribution, Gaussian distribution, Hanning, Hamming, Kaiser, Blackman, and Boxcar.

A basic form of each function may be defined as follows, and when applied to the curve fitting model according to the present disclosure, a weight may be multiplied by the function below.

i) The Blackman function represents the function $$C(k) = 0.42 - 0.5\cos\left(\frac{2\pi k}{N-1}\right) + 0.08\cos\left(\frac{4\pi k}{N-1}\right)$$

(C: curve, N: curve length, k: position index of the curve).

ii) The Gaussian function represents the function $$C(k) = e^{-0.5\left(\frac{k-M}{\sigma M}\right)^2}$$

(C: curve, M: curve length, σ: distribution range of the curve, k: position index of the curve).

iii) The Hamming function represents the function $$C(k) = 0.54 - 0.46\cos\frac{2\pi k}{N-1}$$

(C: curve, N: curve length, k: position index of the curve).

iv) The Hanning function represents the function $$C(k) = 0.5 \times \left[1 - \cos\frac{2\pi k}{N-1}\right]$$

C: curve, N: curve length, k: position index of the curve).

v) The Kaiser function represents the function $$C(k) = \frac{Io\left(\pi\alpha \times \sqrt{1 - \left(\frac{2k}{N-1} - 1\right)^2}\right)}{Io(\pi\alpha)}$$

(C: curve, N: curve length, k: position index of the curve, Io: modified Bessel function of the first kind of order 0, a: distribution range of the curve).

vi) The Boxcar function represents the function C(k)=H (k−a)−H(k−) (C: curve, H: Heaviside function, a, b: both endpoints of the function, k: position index of the curve).

More than one function may be combined to represent a single curve. In the present specification, a curve may represent a graph of a specific function, and for example, the bell-shaped curve may be a curve representing a bell-shaped function.

Equations 1 to 3 above are for explaining the curve fitting model according to the present disclosure, and the present disclosure may include a curve fitting model representing a vascular phase and a Kupffer phase without limitation.

Since Equations 2 and 3 are a combination of functions 1 and 2 through the sum operation, it is difficult to obtain a time intensity curve of only second function, and accordingly, it is difficult to represent a time intensity curve of only Kupffer phase. Therefore, as described below, a difference (−) operation can be performed.

In operation S340, the display unit 140 may display a curve fitting model.

In operation S350, the curve fitting model (second curve) may be stored in the storage 150.

In operation S360, the parameter may be obtained based on the curve fitting model (second curve).

Although it is shown in FIG. 3 that the process of obtaining the first curve is performed before the process of obtaining the second curve, the present disclosure is not limited thereto, and the process of obtaining the second curve using the second contrast agent may be performed before the process of obtaining the first curve.

Figure 4A:
FIG. 4A illustrates a contrast enhanced ultrasound image of an object injected with a first contrast agent in accordance with an embodiment of the present disclosure.
Figure 4B:
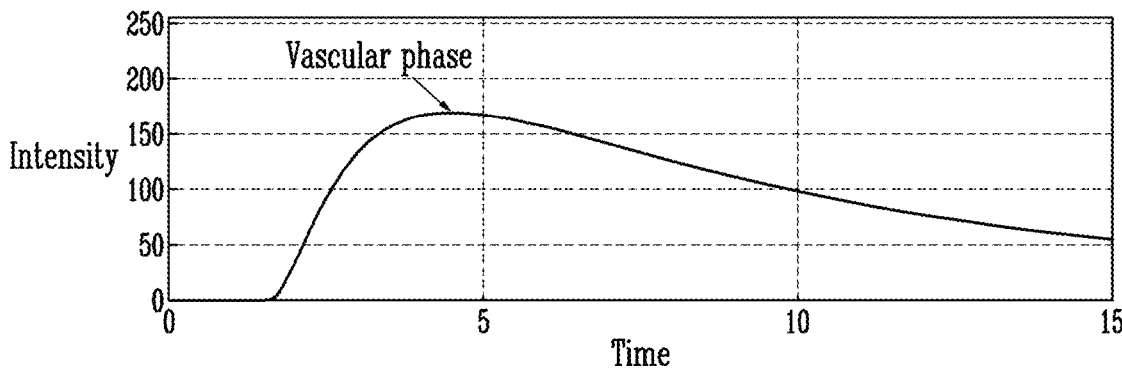
FIG. 4B illustrates a curve fitting model of an object injected with a first contrast agent in accordance with an embodiment of the present disclosure.

FIG. 4A illustrates a contrast enhanced ultrasound image of an object injected with a first contrast agent in accordance with an embodiment of the present disclosure, and FIG. 4B illustrates a curve fitting model of an object injected with a first contrast agent in accordance with an embodiment of the present disclosure.

The left diagram of FIG. 4A shows a contrast enhanced ultrasound image after the first contrast agent is injected, and the right diagram of FIG. 4A shows a B-mode image at the same position as the left diagram.

A pure angiographic contrast agent may be used as the first contrast agent. Pure angiographic contrast agents are supplied to the liver dually through the hepatic artery (25-30%) and the portal vein (70-75%). Therefore, three-stage vascular phases of an arterial phase, a portal venous phase, and a late phase may be observed in a contrast enhanced image using a pure angiographic contrast agent. The arterial phase lasts from 20 to up to 45 seconds after contrast agent injection, the portal venous phase lasts up to 2 minutes after contrast agent injection, and the late phase lasts up to 5 minutes after contrast agent injection. Pure angiographic contrast agents do not migrate into the cell interstitial space, producing pure vascular images.

Representative pure angiographic contrast agents include Sonovue (Bracco SpA, Italy), Definity (Lantheus Medical Imaging, USA), and Optison (GE Healthcare, USA). Sonovue is a microbubble that contains sulfur hexafluoride (SF6) gas in a 2-10 μm phopholipidic monolayer shell, is less phagocytic by surrounding cells, and is mainly used to evaluate blood vessel characteristics as it stays in large and small blood vessels.

FIG. 4B illustrates a curve fitting model of an object injected with a first contrast agent in accordance with an embodiment of the present disclosure, and the curve fitting model of the object injected with the first contrast agent may be a bell-shaped curve. The bell-shaped curves include normal distribution, log-normal distribution, Gaussian distribution, Hanning curve, and the like, and curves representing functions such as Hamming, Kaiser, Blackman, and Boxcar.

Figure 5A:
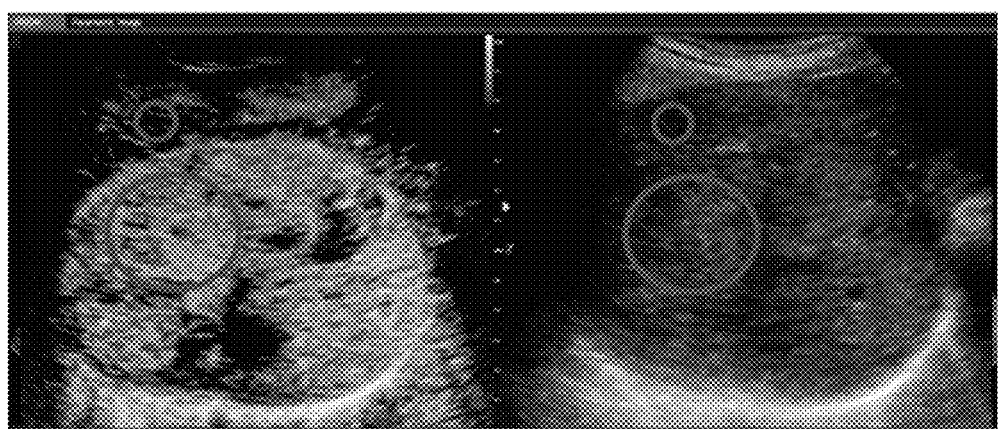
FIG. 5A illustrates a contrast enhanced ultrasound image of an object injected with a second contrast agent in accordance with an embodiment of the present disclosure.
Figure 5B:
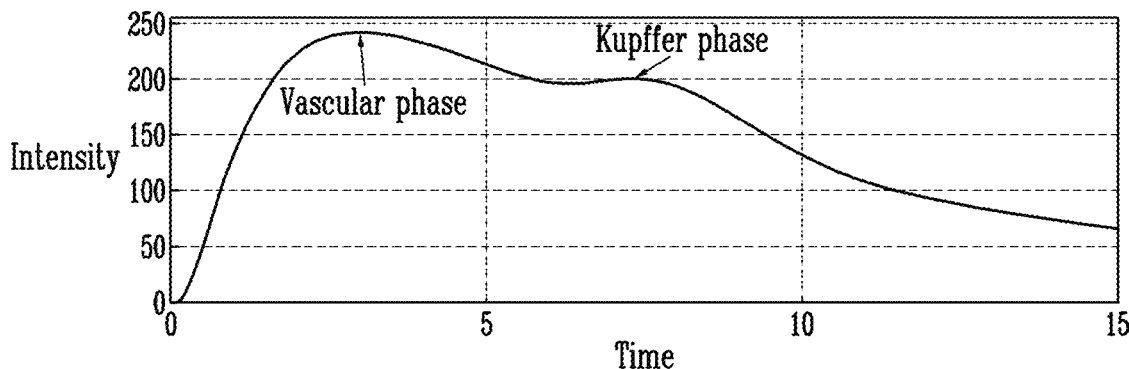
FIG. 5B illustrates a curve fitting model of an object injected with a second contrast agent in accordance with an embodiment of the present disclosure.

FIG. 5A illustrates a contrast enhanced ultrasound image of an object injected with a second contrast agent in accordance with an embodiment of the present disclosure, and FIG. 5B illustrates a curve fitting model of an object injected with a second contrast agent in accordance with an embodiment of the present disclosure.

The left diagram of FIG. 5A shows a contrast enhanced ultrasound image after the second contrast agent is injected, and the right diagram of FIG. 5A shows a B-mode image at the same position as the left diagram.

FIG. 5B shows a curve fitting model of an object injected with a second contrast agent in accordance with an embodiment of the present disclosure, and the curve fitting model of the object into which the second contrast agent is injected may be a bell-shaped curve. The bell-shaped curves include normal distribution, log-normal distribution, Gaussian distribution, Hanning curve, and the like, and curves representing functions such as Hamming, Kaiser, Blackman, and Boxcar. Bell-shaped curves include specifically a double bell-shaped curve or a dual peak or bimodal curve.

The second contrast agent may be a Sonazoid as a Kupffer contrast agent. Sonazoid contains perflubutane gas in a lipid shell. Sonazoids are similar in size to Sonovue, so they can generate blood vessel images, and at the same time, they are phagocytosed by macrophage Kupffer cells in the liver and have the characteristic of showing echogenicity that lasts for several tens of minutes or more in the liver parenchyma.

Accordingly, after injection of Sonazoid, contrast enhancement appears in two stages. In other words, the vascular phase (arterial phase, −30 sec; portal venous phase, −120 sec and delay phase) appears in the first 1-2 minutes after Sonazoid injection, and the Kupffer phase appears about 10-15 minutes after Sonazoid injection.

Kupffer phase appears because Sonazoids are phagocytosed by Kupffer cells in the liver parenchyma about 10 minutes after Sonazoid injection. In cases where normal Kupffer cells do not exist, such as liver cancer cells, since Sonazoids are not phagocytosed, contrast enhancement does not occur in the Kupffer phase and may appear black in areas with lesions. Accordingly, it is possible to diagnose liver cancer based on Sonazoid contrast enhanced ultrasound images.

Meanwhile, the curve fitting model of the object injected with the second contrast agent can be modeled according to Equation 2 below.

$$I_K(t) = C_0 + \frac{C_1}{\sqrt{2\pi}\,\sigma_1(t-t_0)} e^{\frac{-[\ln(t-t_0)-\mu_1]^2}{2\sigma_1^2}} + \qquad \text{[Equation 2]}$$

$$\frac{C_2}{\sqrt{2\pi}\,\sigma_2} e^{\frac{-[(t-t_0)-\mu_2]^2}{2\sigma_2^2}}, \; t > t_0$$

In Equation 2 above, first function $$\left( \frac{C_1}{\sqrt{2\pi}\,\sigma_1(t-t_0)} e^{\frac{-[\ln(t-t_0)-\mu_1]^2}{2\sigma_1^2}}, \; t > t_0 \right)$$

represents the vascular phase and may be a log-normal distribution function. In Equation 2, second function $$\left( \frac{C_2}{\sqrt{2\pi}\,\sigma_2} e^{\frac{-[(t-t_0)-\mu_2]^2}{2\sigma_2^2}}, \; t > t_0 \right)$$

represents the Kupffer phase and may be a normal distribution function.

The curve fitting model according to Equation 2 above may be a model in which first function representing the vascular phase and second function representing the Kupffer phase are combined. At this time, since first function and second function are combined by sum operation, it is difficult to obtain a curve fitting model of second function alone, and accordingly, it is difficult to represent the curve fitting model of only the Kupffer phase.

Meanwhile, the pattern of the vascular phase of the Sonazoid contrast enhanced ultrasound image is similar to the pattern of the vascular phase of the Sonovue contrast enhanced ultrasound image, and the curve fitting model of the vascular phase of the Sonovue contrast enhanced ultrasound image can be modeled with first function $$\left( \frac{C_1}{\sqrt{2\pi}\,\sigma_1(t-t_0)} e^{\frac{-[\ln(t-t_0)-\mu_1]^2}{2\sigma_1^2}}, \; t > t_0 \right).$$

Therefore, if first function is subtracted from Equation 2, second function, i.e., the curve fitting model of only the Kupffer phase can be obtained. In the present disclosure, in order to obtain the value of first function, the Sonovue contrast agent is injected into the object and the echo signal value is obtained. By subtracting the value of first function from the value of second function, the curve fitting model of only the Kupffer phase can be obtained.

Equation 3 below is a combination of a function representing the vascular phase and a function representing the Kupffer phase, as in Equation 2 above, so that the curve fitting model of only the Kupffer phase can be obtained through Equation 3 as in Equation 2.

$$I_K(t) = C_0 + \frac{C_1}{\sqrt{2\pi}\,\sigma_1(t-t_0)} e^{\frac{-[\ln(t-t_0)-\mu_1]^2}{2\sigma_1^2}} + C_3 \mathrm{Sin}[C_4(t-t_0)], \qquad \text{[Equation 3]}$$

$$t > t_0 \;\; \& \;\; C_4(t-t_0) \le \frac{\pi}{2}$$

According to the curve fitting models of Equations 2 and 3, since the second curve includes the curve representing the Kupffer phase, even if there is no difference operation between the first curve and the second curve, the curve representing the Kupffer phase can be obtained even with the second curve itself. In other words, the user can recognize the Kupffer phase only with the second curve without the difference operation between the first and second curves.

Figure 6:
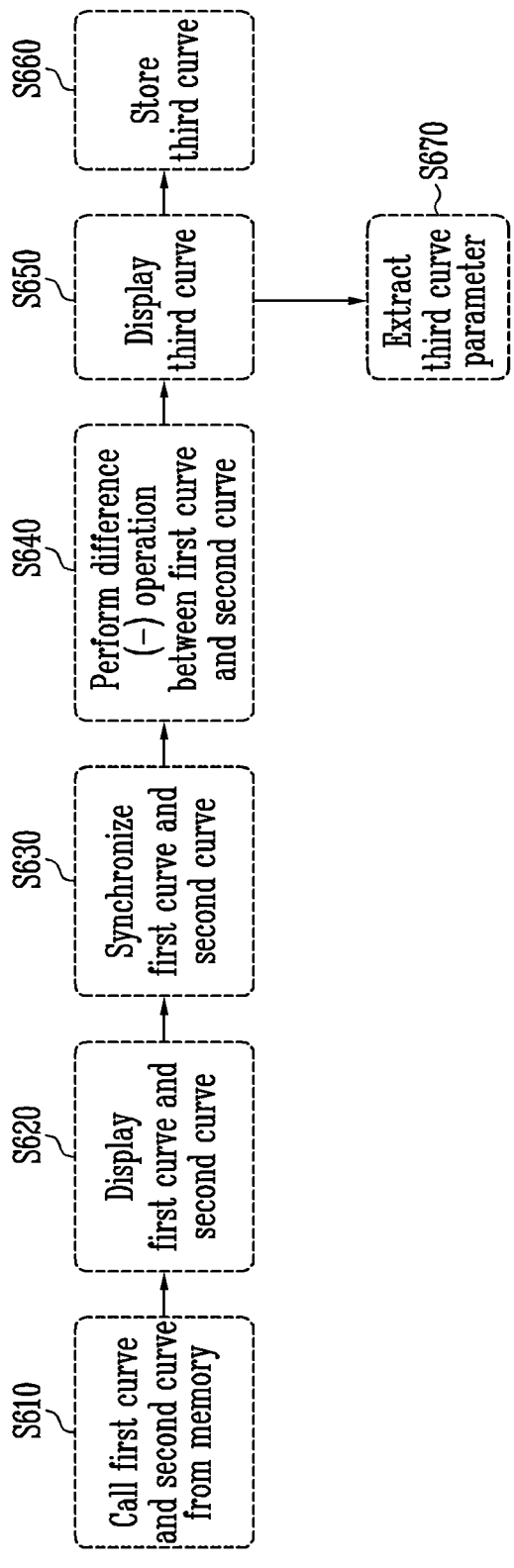
FIG. 6 is a flowchart illustrating an operating method of an ultrasound imaging apparatus in accordance with a third embodiment of the present disclosure.

FIG. 6 is a flowchart illustrating an operating method of an ultrasound imaging apparatus in accordance with a third embodiment of the present disclosure.

Referring to FIG. 6, the third curve can be obtained using the first curve and the second curve. In operation S610, the first curve and the second curve may be called at the storage 150.

In operation S620, the first curve and the second curve may be displayed on the display unit 140.

In operation S630, the first curve and the second curve may be synchronized with each other. The units of the first curve and the second curve may be converted into dB to adjust the scale of both curves (normalization), and the time axes of the first curve and the second curve may be synchronized (time synchronization). Although this is not an essential process, it may be performed for a difference (−) operation between the first curve and the second curve in operation S640.

In operation S650, the result of the difference (−) operation may be displayed. The result of performing the difference operation may appear as a third curve.

In operation S660, the third curve may be stored in the storage 150.

In operation S670, the parameter may be obtained based on the third curve.

FIG. 7 is a diagram illustrating a difference (−) operation method of an ultrasound imaging apparatus in accordance with an embodiment of the present disclosure.

Figure 7A:
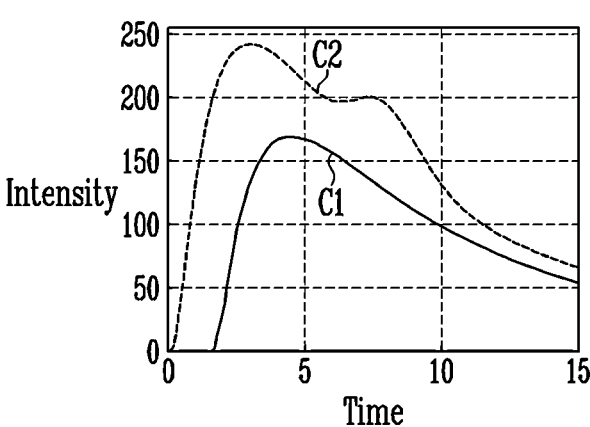
FIG. 7A is a graph illustrating a first curve C1 and a second curve C2 before being synchronized.

FIG. 7A is a graph illustrating a first curve C1 and a second curve C2 before being synchronized. The first curve C1 and the second curve C2 may be called from the storage 150. The first curve C1 is a time intensity curve obtained after injecting the first contrast agent into the object, and the second curve C2 is a time intensity curve obtained after injecting the second contrast agent into the object.

Figure 7B:
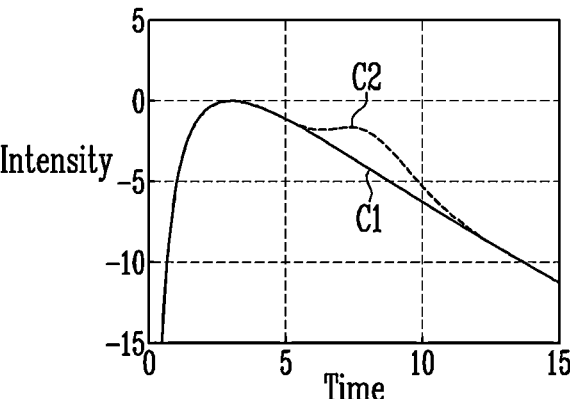
FIG. 7B is a graph illustrating synchronized first curve C1 and second curve C2.

FIG. 7B is a graph illustrating synchronized first curve C1 and second curve C2. Units of the first curve C1 and the second curve C2 may be converted into dB units. The sizes of the first curve C1 and the second curve C2 may be synchronized by converting the first curve C1 and the second curve C2 in units of dB.

The size of the first curve C1 and the second curve C2 may be, based on the highest peak point of the first curve C1 and the second curve C2, by re-adjusting the first curve C1 or the second curve C2 or by providing an offset value, synchronized by setting a difference between the first curve C1 and the second curve C2 to be 0 dB.

The time of the first curve C1 and the second curve C2 may be, based on the highest peak point of the first curve C1 and the second curve C2, by re-adjusting the first curve C1 or the second curve C2 or by providing an offset value, synchronized by setting a difference between the first curve C1 and the second curve C2 to be 0 dB.

Synchronization of the first curve C1 and the second curve C2 may be performed not only at the peak part of each curve, but also at an arbitrary point that can be a reference point, such as the starting point of the first curve C1 and the second curve C2 (first rising point), and the present disclosure is not limited to reference points of synchronization.

Figure 7C:
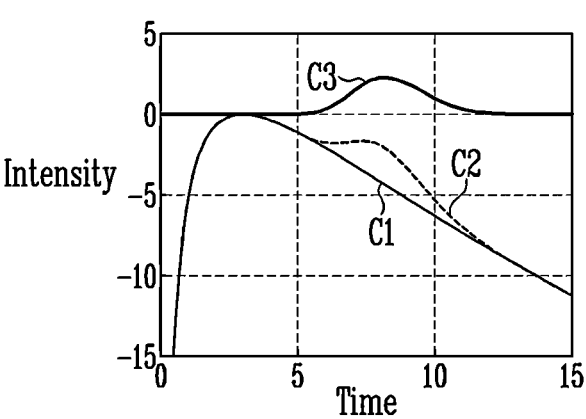
FIG. 7C is a diagram illustrating a third curve C3 derived through a difference (–) operation between the synchronized first curve C1 and second curve C2.

FIG. 7C is a diagram illustrating a third curve C3 derived through a difference (−) operation between synchronized first curve C1 and second curve C2.

Since the result of the difference operation may be a negative value, an operation such as applying a correction value (offset) or an absolute value may be additionally performed so that the result of the difference operation does not become a negative value. The difference between the first curve C1 and the second curve C2 may be a positive value.

Figure 7D:
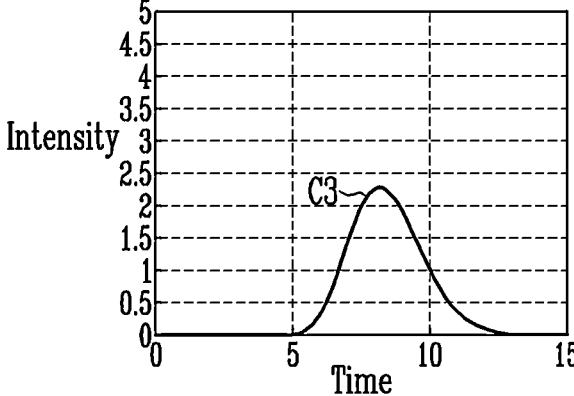
FIG. 7D is a diagram illustrating the third curve C3.

FIG. 7D is a diagram illustrating a third curve C3. The third curve C3 may clearly represent the Kupffer phase.

Figure 8:
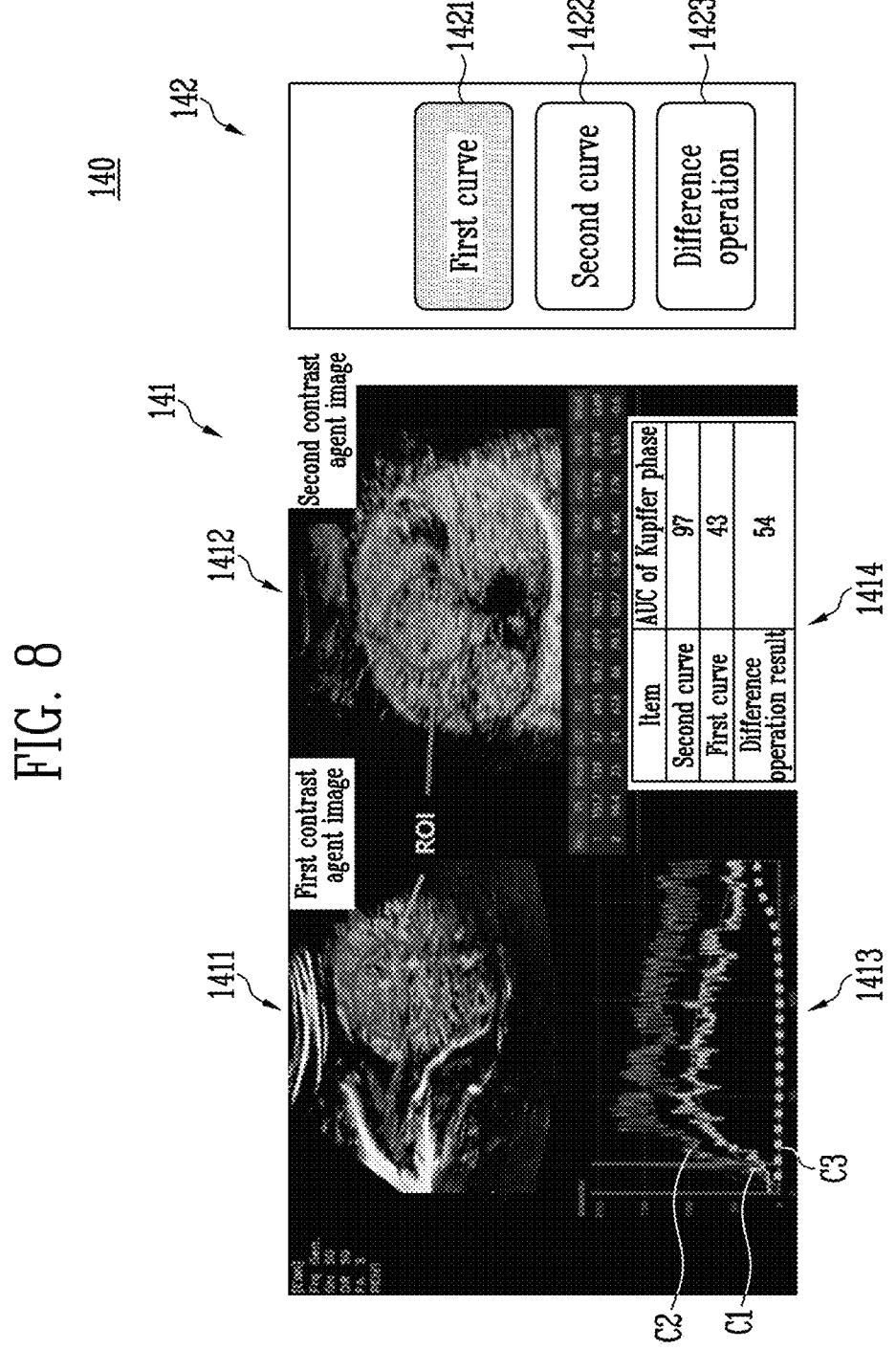
FIG. 8 is a diagram illustrating a display unit 140 of an ultrasound imaging apparatus in accordance with an embodiment of the present disclosure.

FIG. 8 is a diagram illustrating a display unit 140 of an ultrasound imaging apparatus in accordance with an embodiment of the present disclosure.

The display unit 140 may include a first display unit 141 and a second display unit 142. The first display unit 141 displays ultrasound images and curves. The second display unit 142 is a case where the input unit 170 is configured as a touch screen, and the second display unit 142 may be used as an input device capable of inputting information by a user's touch in addition to an output device.

A first contrast agent image part 1411 is a diagram illustrating a contrast enhanced ultrasound image (a first contrast agent image) after a first contrast agent is injected, a second contrast agent image part 1412 is a diagram illustrating a contrast enhanced ultrasound image (a second contrast agent image) after a second contrast agent is injected, a curve part 1413 is a diagram illustrating a first curve C1, a second curve C2, and a third curve C3, and a result part 1414 is a diagram illustrating an area under the curve (AUC) value of a first curve C1 and a second curve C2, and a difference operation result of AUC of a curve C1 and a second curve C2, and a second display unit 142.

As shown in FIG. 8, the display unit 140 may display the first display unit 141 including a first contrast agent image, a second contrast agent image, a first curve C1, a second curve C2, a third curve C3, and a table representing the AUC value, and the second display unit 142 at the same time.

The second display unit 142 may include a first curve button 1421, a second curve button 1422, and a difference operation button 1423. When the first curve C1 is stored in the storage 150, the color of the first curve button 1421 can be displayed (color inverted), and the color of the second curve button 1422 may be displayed when the second curve C2 is stored in the storage 150. The displayed color may be changed to another display by which the user can confirm that the curve is stored, and the present disclosure is not limited thereto.

When the first curve button 1421 is pressed, the first curve C1 can be displayed, and when the second curve button 1422 is pressed, the second curve C2 can be displayed. When the difference operation button 1423 is pressed, the difference operation result may be provided.

In addition, when the first curve button 1421 is touched, the first curve C1 is displayed, and when the second curve button 1422 is touched, the second curve C2 is displayed, and a difference operation may be performed at the same time that the second curve C2 is displayed.

Although it is described above that the first curve button 1421 and the second curve button 1422 are displayed in color when the curve is stored, and the curve is displayed when the first curve button 1421 and the second curve button 1422 are pressed, in addition to the first curve button 1421 and the second curve button 1422, a first curve extraction button (not shown) and a second curve extraction button (not shown) for displaying the curve may be separately provided. The first curve button 1421 and the second curve button 1422 are displayed in color when the curve is stored, and the curve may be displayed when the first curve extraction button (not shown) and the second curve extraction button (not shown) are pressed. At this time, when the button corresponding to the displayed curve is touched again, the displayed curve may not be displayed any more.

As an example, the second display unit 142 shows that the first curve button 1421 is displayed in color as a case where the first curve C1 is stored in the storage 150, and the second curve button 1422 is not displayed in color as a case where the second curve C2 is not stored in the storage 150.

Since the second contrast agent can adsorb to Kupffer cells of the liver, the second curve C2 can represent both the vascular phase and the Kupffer phase. However, since the Kupffer cells are absent or few in liver cancer cells, the Kupffer phase may not appear or be weak in cancer cells. Accordingly, when the result of the difference operation between the area of the first curve C1 and the area of the second curve C2 is equal to or less than a certain value, the object may have liver cancer cells.

Although it has been described above that the result of the difference operation is determined by the difference operation of the area under the first curve C1 and the second curve C2 values, the result of the difference operation may be determined by difference operation of parameter values such as PI (Peak Intensity): Max Intensity of curve, TTP (Time to Peak): Time taken to achieve PI, WiR (Wash in Rate: Max.Slope): Time at which the slope of the curve becomes the maximum value before TTP, WoR (Wash out Rate: Min.Slope): Time at which the slope of the curve becomes the minimum value after TTP, T1: Time of intersection of x-axis of WiR, T2: Time of intersection of x-axis of WoR, RT (Rise Time): RT=TTP−T1, FT (Falling Time): FT=T2−TTP, iAUC (Wash in Area Under the Curve): Area obtained by multiplying and adding the curve fit data of the T1~TTP section by each time divided into small pieces, oAUC (Wash out Area Under the Curve): Area obtained by multiplying and adding the curve fit data of the TTP~T2 section by each time divided into small pieces, AUC (Area Under the Curve): AUC=iAUC+oAUC, and MTT (Mean Transit Time): Average time spent within a given volume.

Since the result of the difference operation may be a negative value, an operation such as applying a correction value (offset) or an absolute value may be additionally performed so that the result of the difference operation does not become a negative value.

In the present specification and drawings, a unit of intensity of brightness may be a unit selectable by a user such as linear scale, dB, or power (uncompressed dB), and the present disclosure is not limited to the unit of brightness.

Figure 9A:
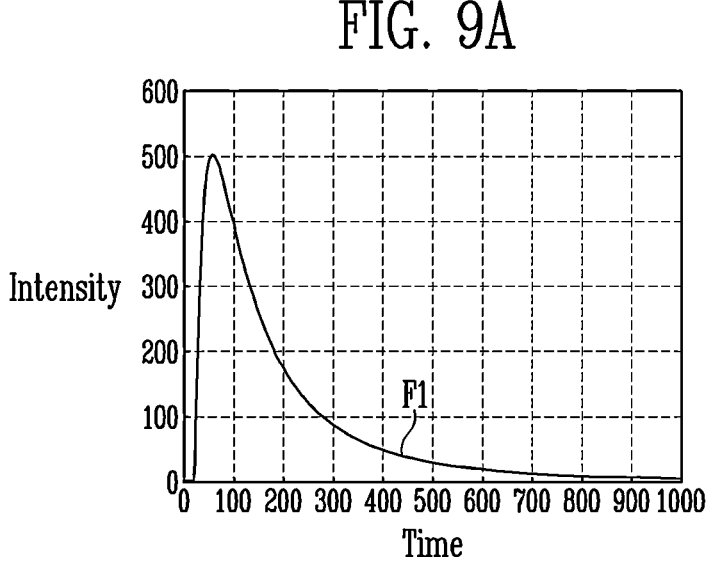
FIG. 9A is a graph illustrating a first function F1.
Figure 9B:
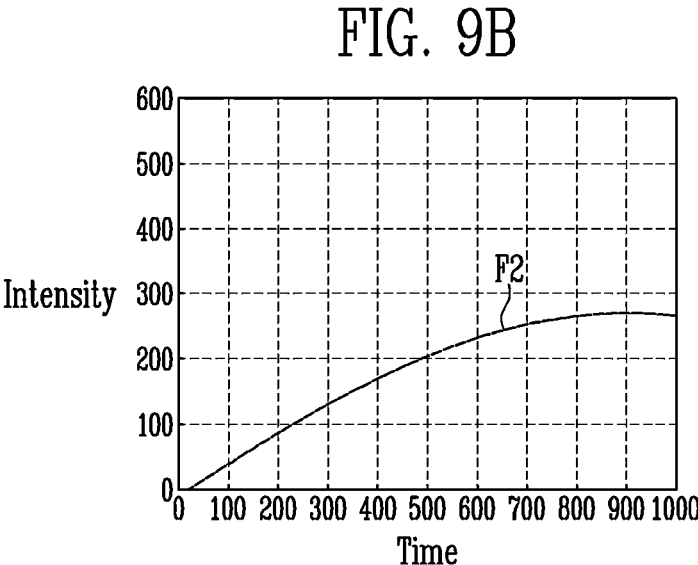
FIG. 9B is a graph illustrating a second function F2.
Figure 9C:
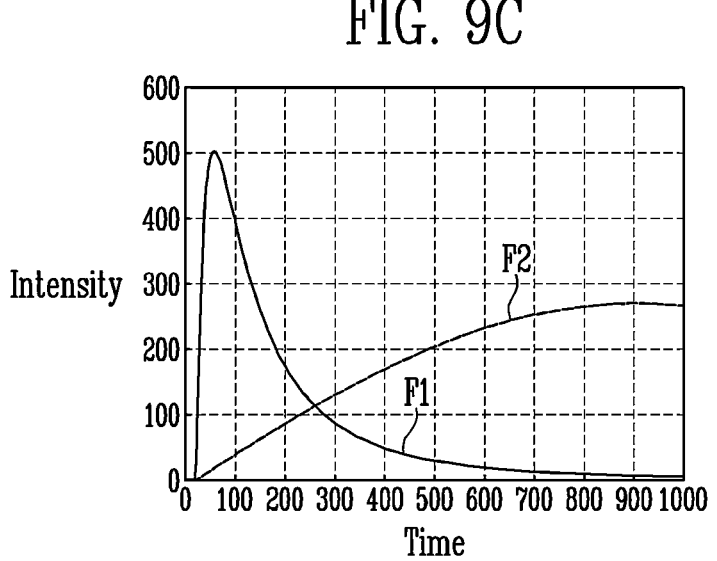
FIG. 9C is a graph illustrating the first function F1 and the second function F2.
Figure 9D:
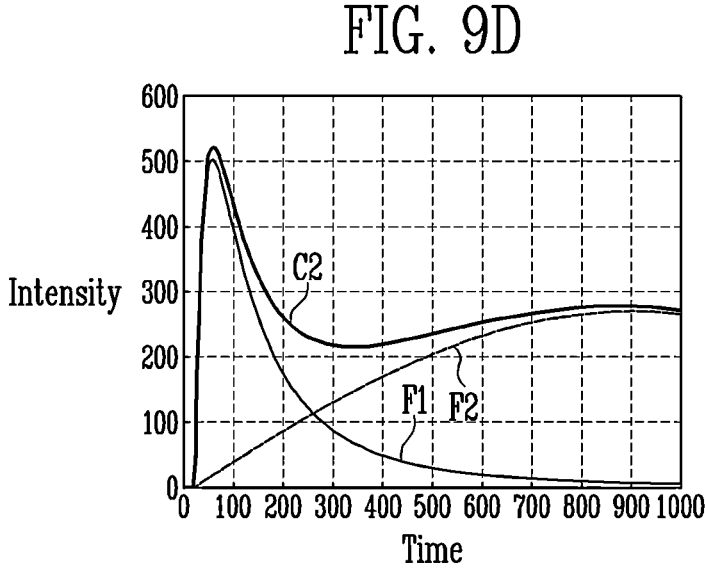
FIG. 9D is a graph illustrating a second curve C2, the first function F1, and the second function F2.

FIG. 9A is a graph illustrating the first function F1. FIG. 9B is a graph illustrating the second function F2. FIG. 9C is a graph illustrating the first function F1 and the second function F2. FIG. 9D is a graph illustrating the second curve C2, the first function F1, and the second function F2.

Figure 10A:
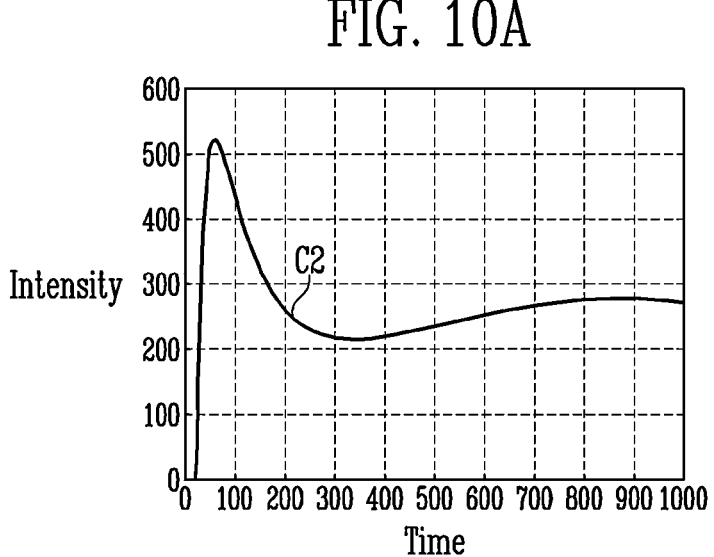
FIG. 10A is a graph illustrating a second curve C2.
Figure 10B:
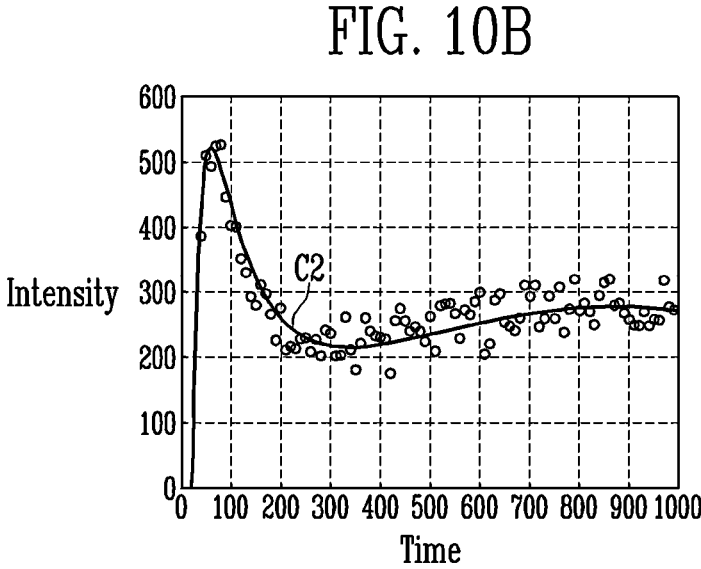
FIG. 10B is a graph illustrating the second curve C2 and brightness data included in the second curve C2.
Figure 10C:
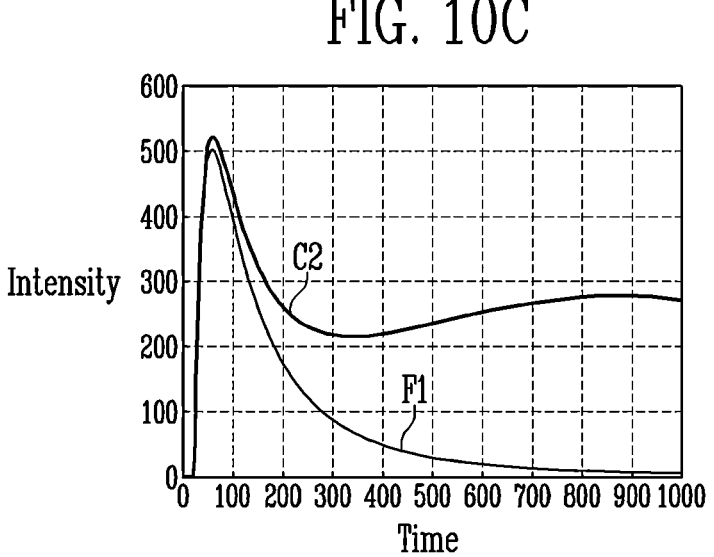
FIG. 10C is a graph illustrating the second curve C2 and a first function F1.
Figure 10D:
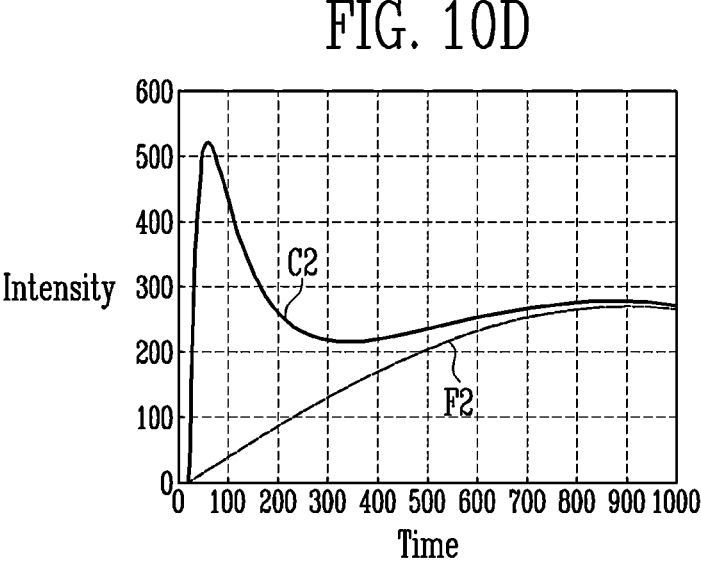
FIG. 10D is a graph illustrating the second curve C2 and a second function F2.

FIG. 10A is a graph illustrating the second curve C2. FIG. 10B is a graph illustrating the second curve C2 and brightness data included in the second curve C2. FIG. 10C is a graph illustrating the second curve C2 and the first function F1. FIG. 10D is a graph illustrating the second curve C2 and the second function F2.

Hereinafter, the first function F1 and the second function F2 may refer to not only the first function F1 and the second function F2, but also graphs representing the first function F1 and the second function F2. In other words, the first function F1 and the second function F2 may refer to the graph of the first function F1 and the graph of the second function F2, respectively.

The curve fitting model of the object injected with the second contrast agent is a model obtained by sum operating the first function F1 representing the vascular phase and the second function F2 representing the Kupffer phase, and the second curve C2 may be derived as a result of the sum operation of the first function F1 and the second function F2.

Referring to FIGS. 9A to 9C, the display unit 140 may display at least one of the first function F1 and the second function F2.

Referring to FIG. 9D, the display unit 140 may display at least one of the first function F1, the second function F2, and the second curve C2.

Referring to FIG. 10A, the display unit 140 may display the second curve C2, and referring to FIG. 10B, the display unit 140 may display the second curve C2 and data values forming the second curve C2 together.

Referring to FIGS. 10C and 10D, the display unit 140 may display the second curve C2 and at least one of the first function F1 and the second function F2.

The curve fitting model according to the first function F1 may be a bell-shaped curve or a periodic function curve such as a Sin function curve or a Cos function curve. In addition, the curve fitting model according to the second function F2 may be a bell-shaped curve or a periodic function curve.

For example, the curves in the form of a periodic function include Sin function curves and Cos function curves, and the bell-shaped curves include curves representing functions such as normal distribution, log-normal distribution, Gaussian distribution, Hanning, Hamming, Kaiser, Blackman, and Boxcar.

The curve fitting model of the second curve C2 may be any one of a bell-shaped curve+bell-shaped curve, a bell-shaped curve+periodic function curve, or a periodic function curve+periodic function curve.

More than one function may be combined to represent a single curve. For example, the log-normal distribution function and the Blackman function may be used together to express the vascular phase in the second curve C2. In addition, the normal distribution function and the Hanning function may be used together to express the Kupffer phase.

Figure 11:
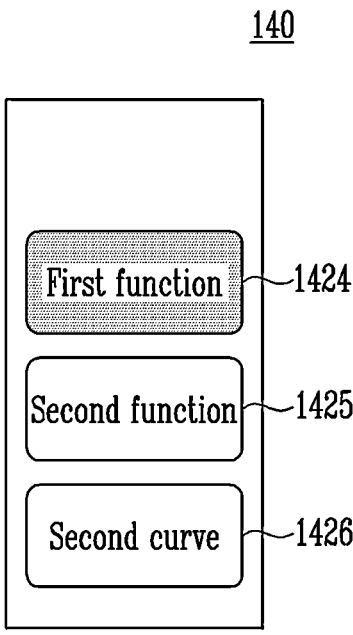
FIG. 11 is a diagram illustrating a first function button 1424, a second function button 1425, and a second curve button 1426.

FIG. 11 is a diagram illustrating a first function button 1424, a second function button 1425, and a second curve button 1426.

Referring to FIG. 11, the display unit 140 may display the first function button 1424, the second function button 1425, and the second curve button 1426. When the first function F1 is stored in the storage 150, the first function button 1424 may display a color (color inverted), when the second function F2 is stored in the storage 150, the second function button 1425 may display a color, and when the second curve C2 is stored in the storage 150, the second curve button 1426 may display a color.

When the first function button 1424 is pressed, the first function F1 may be displayed, when the second function button 1425 is pressed, the second function F2 may be displayed, and when the second curve button 1426 is pressed, the second curve C2 may be displayed.

Although it has been described above that the first function button 1424, the second function button 1425, and the second curve button 1426 display colors when the first function F1, the second function F2 and the second curve C2 are stored, respectively, and that when the first function button 1424, the second function button 1425 and the second curve button 1426 are touched, the first function F1, the second function F2 and the second curve C2 are displayed, in addition to the first function button 1424, the second function button 1425, and the second curve button 1426, a first function extraction button (not shown), a second function extraction button (not shown), and a second curve extraction button (not shown) to control the display of the first function F1, the second function F2, and the second curve C2 may be separately provided.

The first function button 1424, the second function button 1425, and the second curve button 1426 display colors when the first function F1, the second function F2, and the second curve C2 are stored, respectively, and when the first function extraction button (not shown), the second function extraction button (not shown), and the second curve extraction button (not shown) are touched, a curve may be displayed.

The second curve button 1426 of FIG. 11 may have the same configuration as the second curve button 1422 of FIG. 8, and may be configured such that the first function button 1424 and the second function button 1425 are additionally displayed on the second display unit 142 of FIG. 8. In addition, when the second curve button 1422 of FIG. 8 is touched, the first function button 1424, the second function button 1425, and the second curve button 1426 may be displayed. The first function button 1424, the second function button 1425, and the second curve button 1426 may be displayed on the second display unit 142, but the present disclosure is not limited thereto.

The first function button 1424, the second function button 1425, and the second curve button 1426 may be displayed independently, and when the first function button 1424, the second function button 1425, and the second curve button 1426 are touched, corresponding functions or curves may be displayed. When the button corresponding to the displayed function or curve is touched again, the function or curve may no longer be displayed.

As above, the disclosed embodiments have been described with reference to the accompanying drawings. Those skilled in the art to which the present disclosure pertains will understand that the present disclosure can be implemented in a form different from the disclosed embodiments without changing the technical spirit or essential features of the present disclosure. The disclosed embodiments are illustrative and should not be construed as limiting.

What is claimed is:

1. An ultrasound imaging apparatus configured to irradiate ultrasonic waves to an object to which ultrasonic contrast agent is administered, receive an echo signal reflected from the object, and analyze a contrast enhanced (CE) ultrasound image for the object, the ultrasound imaging apparatus comprising:

a display unit;

an image processor configured to set a region of interest in the CE ultrasound image, and generate a first time intensity curve and a second time intensity curve associated with first and second contrast agents, respectively, each of the first and second time intensity curves representing brightness of each frame of the CE ultrasound image within the set region of interest, wherein the image processor is configured to:

generate a first curve representing a vascular phase, the first curve being based on the first time intensity curve obtained from the object to which the first contrast agent is administered and a first curve fitting model representing a tendency of the first time intensity curve;

generate a second curve representing the vascular phase followed by a Kupffer phase, the second curve being based on the second time intensity curve obtained from the object to which the second contrast agent is administered and a second curve fitting model representing a tendency of the second time intensity curve; and generate and display, through the display unit, a third curve as the Kupffer phase, the third curve representing a difference over time between the first curve and the second curve, wherein particles in the first contrast agent are weakly phagocytosed by Kupffer cells in the object compared to particles in the second contrast agent, and wherein the particles in the second contrast agent are strongly phagocytosed by the Kupffer cells in the object compared to the particles in the first contrast agent.

2. The ultrasound imaging apparatus of claim 1, wherein the first curve fitting model of the first curve comprises a bell-shaped curve, and the second curve fitting model of the second curve comprises a bell-shaped curve or a periodic function-shaped curve.

3. The ultrasound imaging apparatus of claim 1, wherein the image processor is configured to generate the third curve representing the difference over time between the first curve and the second curve, after the first curve and the second curve are normalized or time-synchronized.

4. The ultrasound imaging apparatus of claim 1, wherein the display unit is configured to display any one or more of the CE ultrasound image, the first curve, the second curve, and the third curve, and display any one or more of a first curve button indicating that the first curve is stored in a storage, a second curve button indicating that the second curve is stored in the storage, and a difference operation button for displaying the third curve.

5. The ultrasound imaging apparatus of claim 4, wherein the display unit comprises a first display unit and a second display unit, and wherein the first display unit is configured to display any one or more of the CE ultrasound image, the first curve, the second curve, and the third curve, and the second display unit is configured to display any one or more of the first curve button, the second curve button, and the difference operation button.

6. The ultrasound imaging apparatus of claim 5, wherein the second display unit is a touch screen on which information is input by a user's touch, and wherein when the first curve button is touched, the first curve is displayed, when the second curve button is touched, the second curve is displayed, and when the second curve button is displayed or the difference operation button is touched, the third curve is displayed.

7. The ultrasound imaging apparatus of claim 1, wherein the image processor is configured to, through the display unit, display a result of a difference operation between a parameter value of the first curve and another parameter value of the second curve, wherein the parameter values are any one or more of PI (Peak Intensity), TTP (Time to Peak), WiR (Wash in Rate: Max. Slope), WoR (Wash out Rate: Min. Slope), T1 (time of intersection of x-axis of WiR), T2 (time of intersection of x-axis of WoR), RT (Rise Time), FT (Falling Time), iAUC (Wash in Area Under the Curve), oAUC (Wash out Area Under the Curve), AUC (Area Under the Curve), and MTT (Mean Transit Time), and wherein the image processor is configured to determine whether the object includes cancer cells based on the result of the difference operation.

8. The ultrasound imaging apparatus of claim 1, wherein the second contrast agent is a Sonazoid contrast agent.

9. The ultrasound imaging apparatus of claim 1, wherein the display unit is configured to display the first curve and the second curve.

10. An operating method of an ultrasound imaging apparatus configured to irradiate ultrasonic waves to an object, the operating method comprising:

administering a first contrast agent;

setting a region of interest in a first contrast enhanced (CE) ultrasound image;

obtaining a first time intensity curve representing brightness of each frame of the first CE ultrasound image within the region of interest;

administering a second contrast agent;

setting the region of interest in a second CE ultrasound image;

obtaining a second time intensity curve representing brightness of each frame of the second CE ultrasound image within the region of interest;

wherein the method further comprises:

generating a first curve representing a vascular phase, the first curve being based on the first time intensity curve obtained from the object to which the first contrast agent is administered and a first curve fitting model representing a tendency of the first time intensity curve;

generating a second curve representing the vascular phase followed by a Kupffer phase, the second curve being based on the second time intensity curve obtained from the object to which the second contrast agent is administered and a second curve fitting model representing a tendency of the second time intensity curve; and generating and displaying a third curve as the Kupffer phase, the third curve representing a difference over time between the first curve and the second curve, wherein particles in the first contrast agent are weakly phagocytosed by Kupffer cells in the object compared to particles in the second contrast agent, and wherein the particles in the second contrast agent are strongly phagocytosed by the Kupffer cells in the object compared to the particles in the first contrast agent.

11. The operating method of claim 10, wherein the first curve fitting model of the first curve comprises a bell-shaped curve, and the second curve fitting model of the second curve comprises a bell-shaped curve or a periodic function-shaped curve.

12. The operating method of claim 10, wherein the displaying the third curve comprises:

normalizing or time-synchronizing the first curve and the second curve; and generating the third curve representing the difference over time between the normalized or the time-synchronized first curve and the normalized or the time-synchronized second curve.

13. The operating method of claim 10, further comprising:

displaying any one or more of the CE ultrasound images, the first curve, the second curve, and the third curve; and displaying any one or more of a first curve button indicating that the first curve is stored in a storage, a second curve button indicating that the second curve is stored in the storage, and a difference operation button for displaying the third curve.

14. The operating method of claim 13, wherein the display unit comprises a first display unit and a second display unit, wherein any one or more of the CE ultrasound images, the first curve, the second curve, and the third curve are displayed on the first display unit, and any one or more of the first curve button, the second curve button, and the difference operation button are displayed on the second display unit.

15. The operating method of claim 14, wherein the second display unit is a touch screen on which information is input by a user's touch, and wherein when the first curve button is touched, the first curve is displayed, when the second curve button is touched, the second curve is displayed, and when the second curve button is displayed or the difference operation button is touched, the third curve is displayed.

16. The operating method of claim 10, further comprising:

displaying a result of a difference operation between a parameter value of the first curve and another parameter value of the second curve, wherein the parameter values are any one or more of PI (Peak Intensity), TTP (Time to Peak), WiR (Wash in Rate: Max. Slope), WoR (Wash out Rate: Min. Slope), T1 (time of intersection of x-axis of WiR), T2 (time of intersection of x-axis of WoR), RT (Rise Time), FT (Falling Time), iAUC (Wash in Area Under the Curve), oAUC (Wash out Area Under the Curve), AUC (Area Under the Curve), and MTT (Mean Transit Time), and determining whether the object includes cancer cells based on the result of the difference operation.

* * * * *